United States Patent
Shinozaki et al.

(10) Patent No.: US 7,339,050 B2
(45) Date of Patent: Mar. 4, 2008

(54) STRESS-INDUCED PROMOTER AND METHOD OF USING THE SAME

(75) Inventors: Kazuko Shinozaki, Ibaraki (JP); Koji Katsura, Ibaraki (JP); Yusuke Ito, Ibaraki (JP)

(73) Assignee: Japan International Research Center for Agricultural Science, Tsukuba-Shi Ibaraki (JP)

( * ) Notice: Subject to any disclaimer, the term of this patent is extended or adjusted under 35 U.S.C. 154(b) by 145 days.

(21) Appl. No.: 10/550,584

(22) PCT Filed: Mar. 2, 2004

(86) PCT No.: PCT/JP2004/002563

§ 371 (c)(1),
(2), (4) Date: Sep. 22, 2005

(87) PCT Pub. No.: WO2004/085641

PCT Pub. Date: Oct. 7, 2004

(65) Prior Publication Data

US 2006/0206966 A1    Sep. 14, 2006

(51) Int. Cl.
*A01H 1/00* (2006.01)
*C07H 21/04* (2006.01)
*C12N 5/14* (2006.01)
*C12N 15/09* (2006.01)

(52) U.S. Cl. .................. 536/24.1; 435/6; 435/91.4; 435/468; 435/320.1; 536/23.1; 800/278

(58) Field of Classification Search .................. None
See application file for complete search history.

(56) References Cited

OTHER PUBLICATIONS

Kim et al. (Plant Molecular Biology, 24:105-117, 1994).*
Yang et al. (Plant Molecular Biology, 50:379-391, 2002).*
Yamaguchi-Shinozaki et al. (Trends in Plant Science, 10:88-94, 2005).*
Logemann et al. (PNAS, 99:2428-2432, 2002).*
Sasaki et al. (NCBI, GenBank, Sequence Accession No. AP005055, Published Mar. 2002).*
Sasaki et al. (NCBI, GenBank, Sequence Accession No. AP005055, Published Nov. 2004).*
Dubouzet et al. (The Plant Journal, 33:751-763, 2003).*

* cited by examiner

*Primary Examiner*—Phuong T. Bui
*Assistant Examiner*—Vinod Kumar
(74) *Attorney, Agent, or Firm*—Davidson, Davidson & Kappel, LLC

(57) ABSTRACT

This invention provides a stress-inducible promoter that effectively functions in monocotyledonous plants such as rice, and environmental stress-tolerant plants using the promoter. Such promoter is derived from rice and consists of the following DNA (a) or (b): (a) DNA that consists of the nucleotide sequence as shown in SEQ ID NO: 1 or 10; or (b) DNA that hybridizes under stringent conditions with DNA consisting of a nucleotide sequence that is complementary to the DNA consisting of the nucleotide sequence as shown in SEQ ID NO: 1 or 10 and that expresses stress-inducible promoter activity. Such environmental stress-tolerant plant has had such promoter introduced therein.

12 Claims, 9 Drawing Sheets
(3 of 9 Drawing Sheet(s) Filed in Color)

Fig. 2

LIP 9

```
          10         20         30         40         50         60
       TCATCAGCTA TCATCAAAGC GAAGGAAAGA AAGAAAAATA AAAGGAAAAG AACTGGCTGG
          70         80         90        100        110        120
       AAATTAGAGA AGCCCCGGAC GACTCGATCT GGGGGTCGCA AATTAATCAG TGTGATCAAC Myb
         130        140        150        160        170        180
       AGGGATAACT TATCCCGTCC GACCAAATCC ACCAACCAAA CCAAGACCCG ATTTGTTAGG
         190        200        210        220        230        240
       CTGTGAAAGA CGGATCAGTG GGACCCTGAT CTACGGACCC CATATGTCAC CGTCCAGGTC
                                                          Myc
         250        260        270        280        290        300
       TCTGGATCTC TCCCGTCGTC CTAATCAGAC ACCGCGCGCG CGGTGCCGTC GCTCTCGAGC
         310        320        330        340        350        360
       CGTGTCCCGC TCCCAACTCG TCACAAAAGC GATCACAGAC TCTTCCTTCC TCTGCTGGGA
         370        380        390        400        410        420
       GAGAAGAAAA ATTGGCCGCC ATGATGCCGA TAAAGAGGAA AAAGGGATGA GAATCCGATG
         430        440        450        460        470        480
       GAAAAAAACT GATGTTAATC TATCGCTACT GCTGCGCACT AAGACGAATC GTATCCGAAC
         490        500        510        520        530        540
       AAGAAACGCT TACGTTACTG TTCCTAAATG GATCGCTCCG CTCATCACTT AACCAAAAAT
         550        560        570        580        590        600
       CGATTAGGAA ATTGACGGAC AGCGACGCCC GAAGCCAAGT GTCTCGTCGC GTAGGCGTCG
                                                     Myc
         610        620        630        640        650        660
       AGGCCTCGAA GCAGAGGGAG CGGAGAGGCG GACGCGCCGC CCACGCCTCC TCTCCCTCGG
         670        680        690        700        710        720
       TGACACGGCC GTCTGGCTCC ACATGGCGCC GACCTCTCCC GATGCGTCCA CCCGTCCCGA
                                 Myc        DRE
         730        740        750        760        770        780
       GGCACCGCCA CGTCGGAACC AGCCGGCCGC CCCACGCGAT TGCCGACACG CGTCGCGGCG
                                                              DRE
         790        800        810        820        830        840
       CCACTGGCTC ACCCGCTGCC TGCCTCTGCC TGCCCCCCAT CTCGTCGCCA TTTCCCGCCC
         850        860        870        880        890        900
       ACGCTTCTTG TCCTCGCGTC GCCTACGCGT ACGTACGATA CAAACGCCGC ACCTTTCGAT
         910        920        930        940        950        960
       CCCCTCCGCT ATATAAGGAG GGCATCTGCC TCGCCACCTT CTTCATCCGA AAGCAAAAGC
                       TATA
         970        980        990       1000       1010       1020
       GACTCGTCAC AGCTCAAACA AGTCAAGAGC GAATAGTTCT TGCTGATCTG TTGTTTGATT
        1030       1040       1050       1060       1070       1080
       ACTTTAGTTC TCGAGAGGCT TTAGCTGAAT CCATCGATCA TGGAGGATGA GAGGAACA..
                                                  ORF
```

LIP 9
ORF

■ DRE (A/GCCGAC)   ▨ Myb   ▨ Myc   ▮ TATA

LIP9: Gus construct

Fig. 5
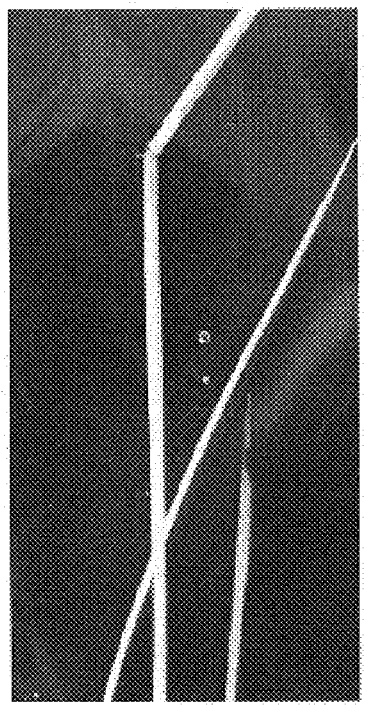
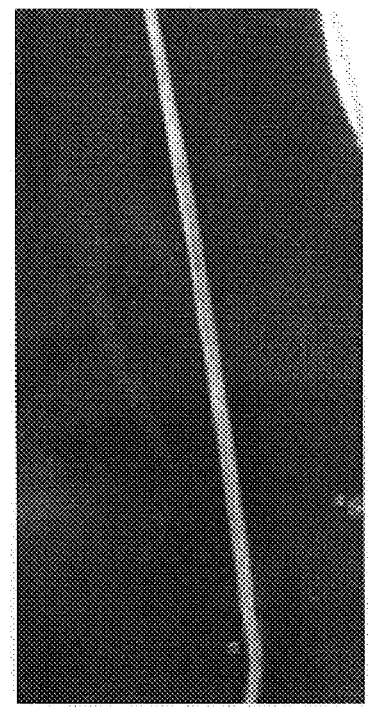
Leaves
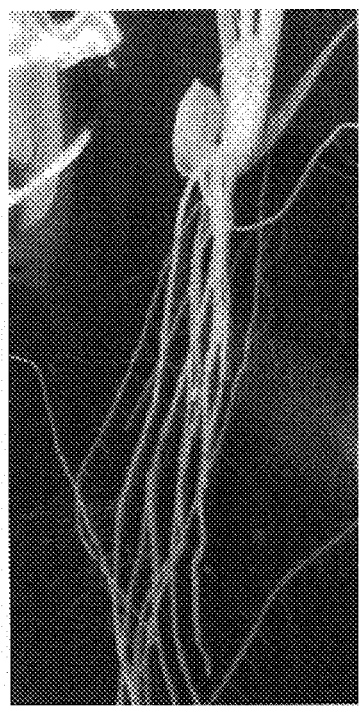
Roots
control      Salt stress

Fig. 7

WSI724

```
          10         20         30         40         50         60
AGCCGTGGAAGTCCAACCTGCAGGCTCAGGCTGCAGATCGCCCAAGGCGCACTTGCCTCC
          70         80         90        100        110        120
ACGATGGCTTGTCCTCAACCGCTCGGAAGGCGAGATCCAATTGGCAATTTGTTCAACGCA
         130        140        150        160        170        180
GGGAGAGAGGAGGAGACTGGAACGGGATCATTGGACATTGGTTGATGAATTGCAATTTGG
         190        200        210        220        230        240
ATGACGAGGCCGCGAGGGTCAGACCGTCGGAGAGTGAGATGATGGTTATACAAGTGTACT
         250        260        270        280        290        300
AGTAGGACGGACGGTGGCACCGGCCAGAAGCAGCAGATTTTGTGCAAACGTTGAGCCCGC
         310        320        330        340        350        360
AACACGTGGCCGGCATCGACCCGCTACGACGGACGCAGCGCCCCCCCCCCCCCCCCCCCC
         370 ABRE  380        390        400        410        420
GCGGACCCACGCGGGCCGGCCGCGCTGTCGCCGTGCTGCCGACTACGCCGTCGAAATCAA
         430        440        450        460 DRE  470        480
CGCGTCCGCCTCGATCCTCCCCTGCCGACGCTGTACAAGTGGCGACCAGAAAACACCATG
         490        500        510 DRE  520        530        540
TAGTATTTGATCTCGTCTAAGAGCAAGTTTAATACTATAGTCCACTATTAGCTCCAATTT
         550        560        570        580        590        600
ATTTATAACTGATCTAATAGCCAATTCACACAATAATTGCTTACTATACTATTAATATAT
         610        620        630        640        650        660
GGTCTCACATGTCATACACATATTCCGTCTTGGAGTTCGTGCTGCAGCTGGCTACAGATC
         670        680        690        700        710        720
TGTAGCCCGCTGCTCTTCTCTCAGAGCGAGTATAATAGTACAAACTGGACTGGCGATA
         730        740        750        760        770        780
GGAGAAACACGTCAGCTACAGTGTTGAGCTGGATGAGTGAGAAGAGGAGAGAGAGTGAGA
         790        800        810        820        830        840
GTGGGCGACAATTTTATCGCCGGCTCTAGCACCAGCTTCGAGAGAAAAGTGGTGAGCGCA
         850        860        870        880        890        900
GAGGTTGTGAGCTGCATGTGTGAGACGAAGCTTAAGTTATTTTATTATGATGTGAAGTTG
         910        920        930        940        950        960
ATGGGTCCAGCGTTGCAGGTCATTTATTGTATTCACAAGATGCAAAGAGAGCTACTAGCT
         970        980        990       1000       1010       1020
GAGTTGGATGGAATTAACGCCGGCTGTCTACGCTACTATTAACCTTGCTCTCATCTTTTA
        1030       1040       1050       1060       1070       1080
TCTCATCAAAATATATTTATAGCTGGCTAATAGTCTGCTATCGTACCTGCTCTAATGCAT
        1090       1100       1110       1120       1130       1140
ACGTTTTTTCTCTCTGTGGCAAAACGGTTGGTGCGTTACACGGGGTGCACGAAGCCATGC
        1150       1160       1170       1180       1190       1200
ATCACCCTGCTCAACCCGTCTCCTTTTTTAGCCTAATCTTTTCCTCCTTATCCGATGGGC
        1210       1220       1230       1240       1250       1260
CTTCCGTTTCTCAAGACACCCCCACACCGCCCCGGCCCTCTATAAATACCAACCACGACG
        1270       1280       1290       1300  TATA       1320
AGCCAAGCGAACATCACCACAGCTAGATCATTAGCAATCCATTCCGATCCATCAAATTTC
        1330       1340 FLcDNA   1360
TCTTGAGACCGTAGAGAGAGAGAGAGGCGCCAACCATGGCCGGCATC
                          ➔ ORF
```

WSI724

▬ DRE(A/GCCGAC)   ▬ ABRE(ACGTGG/T)   ▭ TATA box

▬ cDNA            ▬ ORF

STRESS-INDUCED PROMOTER AND METHOD OF USING THE SAME

FIELD OF THE INVENTION

The present invention relates to a stress-inducible promoter derived from rice and a method for using the same.

BACKGROUND OF THE INVENTION

Plants possess tolerance mechanisms to cope with various types of environmental stresses in nature, such as dehydration, high temperature, freezing, or salt stress. As the stress tolerance mechanism has been elucidated at a molecular level in recent years, stress tolerant plants have been produced via biotechnological techniques. For example, it has been shown that stress proteins such as LEA proteins, water channel proteins, or synthases for compatible solutes are induced in cells when they are exposed to stress, thereby protecting the cells from such stress. Thus, research has been attempted in which genes of LEA proteins of barley or detoxification enzymes of tobacco, genes of synthases for osmoregulatory substances (e.g., sugar, proline, or glycine-betaine), or the like are introduced into host plants. Research using genes encoding w-3 fatty acid desaturase of *Arabidopsis thaliana*, the D9-desaturase of blue-green algae, or the like, which are modification enzymes of the cellular membrane lipid, has also been attempted. In such research, a gene was bound to the 35S promoter of the cauliflower mosaic virus and introduced into a plant. The level of stress tolerance of the recombinant plant was, however, unstable, and the expression level of the introduced gene was low. Thus, none of these was put to practical use.

On the other hand, a stress tolerance mechanism is found to be intricately associated with several genes (Shinozaki K, Yamaguchi-Shinozaki K. Plant Physiol., 1997, October; 115(2), pp. 327-334). Accordingly, research whereby a gene that encodes a transcription factor and that also simultaneously activates the expression of the aforementioned several genes is ligated to a constitutive promoter and introduced into a plant, thereby enhancing the plant's stress tolerance, has been attempted (Liu et al., The Plant Cell, 1998, 10: 1391-1406). When expressions of several genes are simultaneously activated, however, the energy of the host plant becomes directed towards the synthesis of the gene product or intracellular metabolism resulting from the gene product. Accordingly, the growth of the plant itself becomes retarded or results in a dwarf.

In contrast, the present inventors isolated from *Arabidopsis thaliana* the DREB1A, DREB1B, DREB1C, DREB2A, and DREB2B genes encoding the transcription factors that bind to a stress-responsive element and specifically activate the transcription of genes located downstream of such element (JP Patent Publication (Unexamined Application) No. 2000-60558). They reported that the introduction of the genes into a plant by ligating them to a stress-inducible rd29A promoter enabled production of a stress-tolerant plant without retarding plant growth (JP Patent Publication (Unexamined Application) No. 2000-116260).

The rd29A promoter is derived from *Arabidopsis thaliana*, which is a dicotyledonous plant. It is able to function in monocotyledonous plants, although its activity level is low. Accordingly, a stress-inducible promoter capable of a high level of activity in monocotyledonous plants has been awaited.

SUMMARY OF THE INVENTION

The present invention is directed to discovering a stress-inducible promoter that can effectively function in monocotyledonous plants such as rice and to providing a novel environmental stress-tolerant plant using such promoter.

The present inventors have conducted concentrated studies in order to attain the above object. As a result, they have succeeded in isolating a potent stress-inducible promoter from the rice genome. They have also found that the environmental stress tolerance of the monocotyledonous plant could be significantly improved with the use of such promoter. This has led to the completion of the present invention.

Specifically, the present invention relates to a stress-inducible promoter derived from rice. More specifically, the promoter consists of the following DNA (a) or (b):

(a) DNA consisting of the nucleotide sequence as shown in SEQ ID NO: 1 or 10; or (b) DNA hybridizing under stringent conditions with DNA consisting of a nucleotide sequence that is complementary to the DNA consisting of a nucleotide sequence as shown in SEQ ID NO: 1 or 10 and expressing stress-inducible promoter activity.

The term "stress" used herein refers to dehydration stress, low temperature stress, or salt stress.

The present invention provides a recombinant vector comprising the aforementioned promoter. The vector may comprise other structural genes or regulatory genes under the control of the promoter according to the present invention. It is particularly preferable that the vector comprises structural genes and/or regulatory genes for enhancing stress tolerance.

Examples of preferable structural genes for enhancing stress tolerance include the P5CS gene, which is a key enzyme for proline synthesis (Yoshiba Y. et al., 1999, BBRC 261), and the AtGolS3 gene for galactinol synthesis (Taji T. et al., 2002, Plant J. 29: 417-426).

Examples of preferable regulatory genes for enhancing stress tolerance include the *Arabidopsis thaliana*-derived DREB transcription factor genes (JP Patent Publication (Unexamined Application) No. 2000-60558), the rice-derived OsDREB transcription factor genes (Japanese Patent Application No. 2001-358268, Dubouzet et al., Plant J. in press), and the NCED gene, which is a key enzyme for the biosynthesis of the plant hormone ABA (Iuchi S. et al., 2001, Plant J. 27: 325-333).

The *Arabidopsis thaliana*-derived DREB transcription factor genes and the rice-derived OsDREB transcription factor genes are particularly preferable. The rice-derived OsDREB transcription factor genes are most preferable.

The present invention provides a transgenic plant that is obtained by introducing the vector of the present invention into a suitable host. According to one embodiment of the present invention, the transgenic plant is obtained by introducing the vector of the present invention into a host plant. In such a case, the host plant is preferably a monocotyledonous plant, and such monocotyledonous plant is preferably rice.

By introducing the promoter of the present invention into plants, the present invention can further provide a method for enhancing stress tolerance in plants. The promoter of the present invention exhibits potent stress-inducible promoter activity that has never been observed in monocotyledonous plants, and thus, the promoter of the present invention is more suitable for enhancing the stress tolerance of monocotyledonous plants.

BRIEF DESCRIPTION OF DRAWINGS

The patent or application file contains at least one drawing executed in color. Copies of this patent or patent application publication with color drawings will be provided by the Office upon request and payment of the necessary fee.

FIG. 2 shows the nucleotide sequence of a0022(LIP9) in its promoter region.

FIG. 5 is a photograph showing the results of GUS staining on transgenic rice prepared by introducing an LIP9 promoter ligated to GUS genes when salt stress is applied.

FIG. 7 shows the nucleotide sequence of a0066(WSI724) in its promoter region.

DETAILED DESCRIPTION OF THE INVENTION

Figure 1:
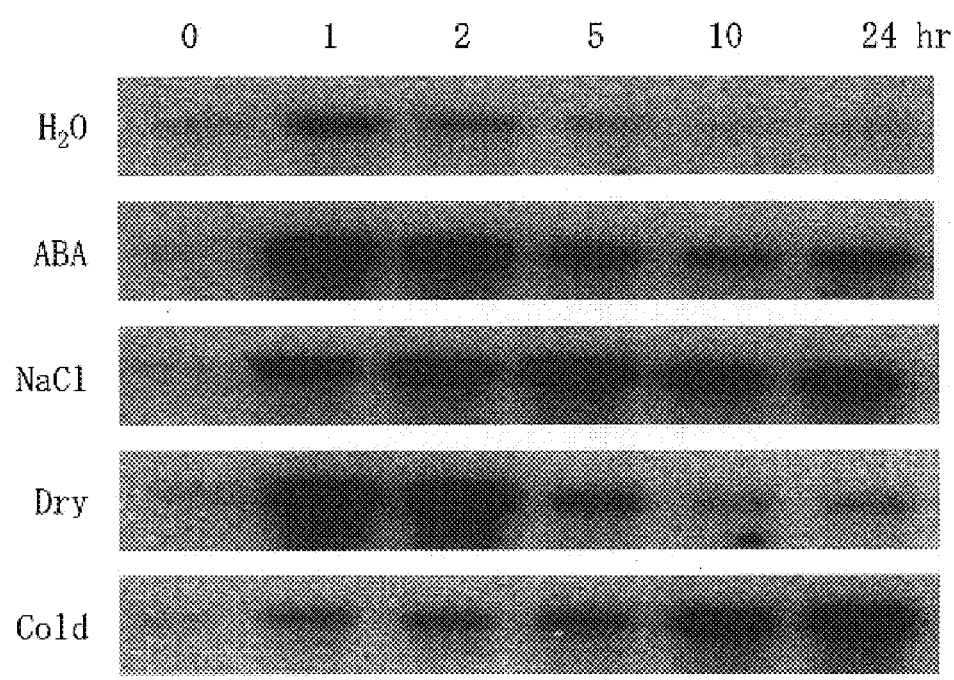
FIG. 1 shows the results of Northern analysis on a0022 (LIP9) when each type of stress is applied.

This description includes part or all of the contents as disclosed in the description of Japanese Patent Application No. 2003-80847, which is a priority document of the present application.

EMBODIMENTS OF THE INVENTION

The promoter of the present invention is a rice-derived promoter, which is induced specifically by environmental stress such as low temperature, dehydration, or salt stress.

1. Identification of the Promoter of the Present Invention

The promoter of the present invention can be identified as follows. Plants that were given stress are compared with plants that were not given stress, and genes that are expressed at significantly different levels (stress-inducible genes) are first screened for. Based on the genome information, a sequence that is considered to be a promoter of the gene is then screened for.

A process for identifying the promoter of the present invention is hereafter described.

1.1 Preparation of mRNA

At the outset, mRNA for screening for the stress-inducible genes is prepared.

A source of mRNA may be a part of a plant such as a leaf, stem, root, or flower or a plant as a whole. Alternatively, a plant obtained by sowing seeds on a solid medium such as GM medium, MS medium, or #3 medium and growing them aseptically may be used. The source may be a callus or a cultured cell of the plant that was aseptically grown.

In this screening process, differences in gene expression levels are observed between plants that were given stress and plants that were not given stress. Thus, it is necessary to prepare mRNAs for each of the plants. A method for applying stress is suitably determined depending on the types of plants to be used. In general, dehydration stress can be applied by growing plants without water for 2 to 4 weeks. Low temperature and freezing stresses can be applied by growing plants at 15 to −10° C. for 1 to 10 days. Salt stress can be applied by growing plants in 100 to 600 mM NaCl for 1 hour to 7 days. In the case of rice, for example, hydroponically grown rice is exposed to low temperature stress (10 to −4° C.), salt stress (150 to 250 mM NaCl), and dehydration stress (desiccated state).

Plants that were given stress and plants that were not given stress are frozen with liquid nitrogen and ground in a mortar, etc. From the resulting ground material, a crude RNA fraction is extracted by the glyoxal method, the guanidine thiocyanate and cesium chloride method, the lithium chloride and urea method, the proteinase K and deoxyribonuclease method, or the like. From this crude RNA fraction, poly(A)+ RNA (mRNA) can be then obtained by the affinity column method using oligo dT-cellulose, poly U-Sepharose carried on Sepharose 2B, or the like or by the batch method. The resulting mRNA may further be fractionated by sucrose density gradient centrifugation or the like, if necessary.

1.2 Screening for Stress-Inducible Gene

The stress-inducible genes are screened for based on a comparison of differences in gene expression levels between plants that were given stress and plants that were not given stress. Methods for comparing the gene expression levels are not particularly limited, and examples thereof include conventional methods such as RT-PCR, real time PCR, subtraction, differential display, differential hybridization, and cross hybridization.

A method using solid phase samples such as gene chips and cDNA microarrays is especially suitable for implementing the screening procedure because such method can simultaneously detect the expression of several thousands to several tens of thousands of genes qualitatively and quantitatively.

(1) Preparation of cDNA Microarray

The cDNA microarray used in the screening procedure is not particularly limited as long as the cDNA of the monocotyledonous plant (e.g., rice), i.e., a detection target of the promoter, is spotted thereon. An existing array may be used, or an array may be prepared based on conventional methods (e.g., The Plant Cell (2001) 13: 61-72 Seki et al.).

When preparing the cDNA microarray, the cDNA library of the plant of interest should be prepared first. The cDNA library can be produced by conventional methods using mRNA prepared in accordance with the method in (1) as a template. The cDNA to be spotted is not particularly limited as long as it is derived from monocotyledonous plants. From the viewpoint of ease in later analyses of genome databases, cDNA derived from monocotyledonous plants such as rice with advanced genome analysis is preferable. Plants may be in a normal state (without treatment). However, plants are preferably exposed to stress such as dehydration, salt, or low temperature.

When producing the cDNA library, a commercially available kit (e.g. ZAP-cDNA Synthesis Kit, Stratagene) is first used for reverse transcription of mRNA and single-stranded cDNA synthesis. Then, double-stranded cDNA is synthesized using the resulting single-stranded cDNA as a template. Subsequently, an adaptor containing a suitable restriction site is added to the resulting double-stranded cDNA, which is then inserted into a cloning site of a lambda phage vector. The resulting DNA is packaged in vitro using a commercially available kit (e.g., Gigapack III Gold packaging extract (Stratagene)), caused to infect an E. coli host, and then amplified. Thus, the cDNA library of interest can be obtained.

Once the cDNA library is produced, this cDNA or a region with a high specificity in such cDNA (e.g., the UTR region containing no repeating sequence on the 3' side) is amplified by PCR to produce a probe to be immobilized on the array. When probes for all the genes of interest are produced by repeating this procedure, these probes are spotted on a slide glass using a commercially available spotter (e.g., one manufactured by Amersham). Thus, the cDNA microarray of interest is obtained.

(2) Detection of Gene Expression Level

Gene expression levels can be detected by the cDNA microarray as signal intensity obtained when sample mRNA (or cDNA) labeled with a suitable reagent is hybridized with the cDNA probe on the microarray. In general, the expression level of the gene is preferably determined as a comparative value with a suitable control or the ratio of expression levels between two samples to be compared, with respect to the differences in the amount of cDNA probes spotted on the array. In the case of the present screening procedure, mRNA derived from plants that were not given stress (without treatment) is employed as a control, and relative expression levels of mRNA derived from plants that were given stress may be detected in relation thereto.

Detection is carried out as follows. mRNAs of the control and the sample (or cDNA thereof) are labeled with different fluorescent dyes (e.g., Cy3 and Cy5) and hybridized with the cDNA probe on the array. For example, mRNA is extracted from the plants that were given stress and subjected to reverse transcription in the presence of Cy5-labeled dCTP to prepare Cy5-labeled cDNA. Subsequently, mRNA is extracted from plants that were not given stress (without treatment), and Cy3-labeled cDNA is prepared in the same manner. Cy5-labeled cDNA (sample) is mixed with an equivalent amount of Cy3-labeled cDNA (control), and the resultant is hybridized with cDNA on the array. Cy3 may be used for labeling the sample, and Cy5 may be used for labeling the control. Alternatively, other suitable label reagents may also be used.

The obtained fluorescence intensity is read using a fluorescent signal detector and then converted into a numerical value. This numerical value is equivalent to the ratio of the gene expression levels of the sample relative to the control. The fluorescence intensity read using a scanner is optionally subjected to error adjustment or normalization of variances for each sample. Normalization can be carried out based on the genes that are commonly expressed in each sample, such as house keeping genes. Further, a threshold line for reliability may be determined to remove data with low correlation.

(3) Selection of Stress-Inducible Genes

Based on the analytical results by the array, stress-inducible genes are specified as genes that are expressed at significantly different levels between plants that were given stress and plants that were not given stress. The term "significantly different" used herein refers to, for example, an intensity level of 1,000 or higher, and a difference between two plants of three times or more.

(4) Analysis of Expression by Northern Blotting

The thus selected genes are further subjected to Northern analysis and the like. Thus, the expression levels of the genes are confirmed to be enhanced with respect to stress tolerance levels. For example, plants are exposed to various levels of stress such as salt, dehydration, or low temperature stress in the manner described above. RNA is then extracted from the plant and separated by electrophoresis. The separated RNA is transferred to a nitrocellulose membrane and hybridized with a labeled cDNA probe that is specific for the gene. Thus, the expression level thereof can be detected.

If the expression level of the selected gene is enhanced in a stress-dependent manner, it can be confirmed that the gene is stress-inducible. Examples of stress-inducible genes selected from the rice cDNA library include a0022 (LIP9: SEQ ID NO: 2) and a0066 (WSI724: SEQ ID NO: 8) of the present invention. a0022 and a0066 are identification numbers (ID No.) of cDNA immobilized on the microarray.

1.3 Screening for Promoter Sequence (1) Screening of Gene Database

Subsequently, detection software (e.g., Blast) is used to search existing gene databases (e.g., the DDBJ database) for promoter sequences of the stress-inducible genes. Regarding a plant such as rice, the genome of which has been mostly decoded, all promoter sequences controlling specified stress-inducible genes can be searched for by using existing databases. Promoter sequences are selected as regions that are considered to be promoters from among the upstream regions in genome genes that are highly genomically identical to the stress-inducible gene (cDNA). Based on the genome information of stress-inducible genes, for example, the region approximately 1 to 2 kb upstream of the site that is presumed to be an initiation codon for these genes is deduced to be a promoter region.

Some of the conventional stress-inducible promoters have in their sequences cis elements involved with promoter activities, such as dehydration responsive elements (DRE), abscisic acid responsive elements (ABRE), and low temperature responsive elements. When a stress-inducible transcription factor is bound to the cis element, the aforementioned promoter is activated, and the stress-tolerance-imparting genes that are under the control of the promoter are allowed to express. If the cis element is contained in the upstream region that has been screened, accordingly, this region is highly likely to be a stress-inducible promoter.

Thus, the genome information of a gene highly homologous to the aforementioned a0022 (LIP9: SEQ ID NO: 2) was obtained, and a deduced LIP9 promoter sequence (SEQ ID NO: 1) was screened for from the region 1.1 kb upstream thereof. Similarly, a deduced WSI724 promoter sequence (SEQ ID NO: 10) was screened for from the upstream region of a gene highly homologous to a0066 (WSI724: SEQ ID NO: 8).

(2) Confirmation of Functionality of Stress-Inducible Promoter

Subsequently, the functionality of the deduced promoter sequence is confirmed by changes in promoter activity when stress is applied.

At the outset, a primer is produced based on the promoter sequence deduced in the section above. PCR is carried out using genome DNA as a template, and the promoter is cloned. Subsequently, a reporter gene is ligated downstream of the promoter to produce a reporter plasmid. The produced reporter plasmid is then introduced into a plant, thereby investigating the expression of the reporter gene when stress is applied to the plant (preferably its $T_2$ generation). Examples of reporter genes include β-glucuronidase (e.g., GUS: pBI121, Clontech), luciferase gene, and green fluorescent protein gene. GUS is preferable because its activity can be indicated by numerical values and its expression can be visually observed via staining.

1.4 Promoter of the Present Invention

Based on the above, the rice genome-derived LIP9 promoter sequence (SEQ ID NO: 1) was found to be a stress-inducible promoter, which was expressed highly in a dehydration-, low temperature-, or salt stress-dependent manner.

As mentioned above, the LIP9 promoter is induced specifically by every type of stress. The structural and functional features thereof are as follows.

1) The LIP9 promoter comprises in its structure 2 DRE cis elements associated with dehydration stress induction (FIG. 2).

2) The expression level of the LIP9 is high in a plant that allows overexpression of the OsDREB1 gene (Japanese Patent Application No. 2001-358268), which is a rice-derived transcription factor that binds to a DRE cis element and activates the transcription of the gene located downstream thereof.

3) The LIP9 promoter comprises the DRE sequence to which the OsDREB1 protein binds. Accordingly, the LIP9 promoter is deduced to be optimal for overexpression of the OsDREB gene.

Also, the WSI724 gene is a target of the OsDREB gene. Such deduction is made based on the fact that the WSI724 promoter comprises in its structure 2 DRE sequences, and it is made based also on the expression pattern of a0066 when stress is applied (the expression pattern is inducible by dehydration, salt, and low temperature stresses and the rate of induction by low temperature is slower than that by dehydration and salt).

The promoter of the present invention is not limited to DNA consisting of the nucleotide sequence as shown in SEQ ID NO: 1 or 10. The stress-inducible promoter of the present invention includes DNA that hybridizes under stringent conditions with DNA consisting of a nucleotide sequence that is complementary to the DNA consisting of the nucleotide sequence as shown in SEQ ID NO: 1 or 10 as long as such DNA has stress-inducible promoter activity. Under the "stringent conditions," hybridization is carried out in 30%-50% formamide at 37° C. to 50° C. in 6×SSC, and preferably in 50% formamide at 42° C. in 6×SSC.

2. Recombinant Vector

The recombinant vector of the present invention comprises the promoter of the present invention. The vector may comprise other functional structural genes or regulatory genes downstream of the promoter of the present invention. Examples of preferable genes include structural genes and/or regulatory genes for enhancing stress tolerance. The term "functional" refers to a state in which other structural genes or regulatory genes are suitably expressed under the control of the promoter of the present invention.

Structural genes for enhancing stress tolerance encode a protein that plays roles in enhancing plants' tolerance to environmental stress such as dehydration, low temperature, or salt stress. Examples thereof include: LEA proteins; water channel proteins; synthases for compatible solutes; detoxification enzyme of tobacco; synthases for osmoregulatory substances (e.g., sugar, proline, or glycinebetaine); genes encoding w-3 fatty acid desaturase of *Arabidopsis thaliana* and the D9-desaturase of blue-green algae, which are modification enzymes of the cellular membrane lipid; P5CS, which is a key enzyme of proline synthesis; and the AtGolS3 gene for galactinol synthesis.

A regulatory gene for enhancing stress tolerance regulates the activity of a stress-inducible promoter and the expression of genes for imparting stress tolerance, thereby enhancing stress tolerance in plants. Examples thereof include: *Arabidopsis thaliana*-derived transcription factors such as DREB1A, DREB2A, DREB1B, and DREB1C genes (JP Patent Publication (Unexamined Application) No. 2000-60558); rice-derived transcription factors such as OsDREB1A, OsDREB1B, OsDREB1C, OsDREB1D, and OsDREB2A genes (Japanese Patent Application No. 2001-358268); and NCED genes, which are key enzymes for the biosynthesis of the plant hormone ABA.

When the promoter of the present invention comprises a specific cis element, the gene of the transcription factor that binds to the cis element and enhances its promoter activity is particularly preferably ligated downstream of the promoter.

As described above, the LIP9 promoter according to the present invention comprises in its structure 2 DRE sequences. Thus, the DREB or OsDREB gene (for example, OsDREB1A, OsDREB1B, OsDREB1C, OsDREB1D, OsDREB2A, or OsDREB2B gene) is preferably ligated downstream of the LIP9 promoter. The OsDREB gene is most preferable.

Since the WSI724 promoter also comprises 2 DRE sequences and it is deduced to be the target of OsDREB, the DREB or OsDREB gene (for example, OsDREB1A, OsDREB1B, OsDREB1C, OsDREB1D, OsDREB2A, or OsDREB2B gene) is preferably ligated downstream of the WSI724 promoter. The OsDREB gene is most preferable.

The vector of the present invention is constructed so as to be functional by ligating (inserting) the promoter of the present invention or the promoter and another regulatory gene or structural gene to (into) an appropriate vector. The vector into which the promoter is to be inserted is not particularly limited as long as it is capable of replicating genes of interest in a host. For example, plasmid DNA, phage DNA, or the like may be used. Plasmid DNA includes: plasmids for *E. coli* hosts such as pBR322, pBR325, pUC118, and pUC119; plasmids for *Bacillus subtilis* hosts such as pUB110 and pTP5; plasmids for yeast hosts such as YEp13, YEp24, and YCp50; and plasmids for plant cell hosts such as pBI221 and pBI121. Phage DNA includes λ phage DNA and the like. Further, an animal virus vector such as a retrovirus or vaccinia virus vector, or an insect virus vector such as a baculovirus vector, may also be used.

The promoter of the present invention is inserted into a vector by cleaving the purified DNA with an appropriate restriction enzyme and then inserted into the restriction site or the multi-cloning site of an appropriate vector for ligation.

The recombinant vector of the present invention may comprise a splicing signal, poly(A) addition signal, selection marker, ribosome binding sequence (SD sequence) or the like, if so desired. Examples of selection markers are dihydrofolate reductase genes, ampicillin tolerance genes, neomycin tolerance genes, and the like.

3. Transgenic Plant

The transgenic plant of the present invention can be produced by introducing the recombinant vector of the present invention into a host so that promoter activity can be expressed. Hosts are not particularly limited as long as the promoter of the present invention can function therein. Hosts are preferably plants, and the monocotyledonous plants such as rice are particularly preferable.

When plants or plant cells are used as hosts, for example, cells established from rice, maize, wheat, *Arabidopsis thaliana*, tobacco, or carrot or protoplasts prepared from these plants are used. Methods for introducing recombinant vectors into plants include a method of Abel et al., which utilizes polyethylene glycol (Abel, H. et al. Plant J. 5:421-427, 1994), and electroporation.

4. Stress Tolerant Transgenic Plant (1) Production of Transgenic Plant

Structural genes and/or regulatory genes for enhancing stress tolerance are introduced into plants so as to be under the control of the promoter of the present invention. Thus, functional transgenic plants with enhanced tolerance to environmental stress such as low temperature, freezing, or dehydration stress can be produced. An example of particularly preferable host plants are monocotyledonous plants.

A method for introducing the promoter of the present invention, etc. into a host plant includes indirect introduction such as the *Agrobacterium* infection method and direct introduction such as the particle gun method, the polyethylene glycol method, the liposome method, and the microinjection method. Up to the present, it had been difficult to carry out the *Agrobacterium* infection method to produce transgenic plants from monocotyledonous plants such as rice. However, the addition of acetosyringon enabled *Agrobacterium* to infect rice. Thus, the *Agrobacterium* infection method became applicable for monocotyledonous plants.

Production of transgenic plants using *Agrobacterium* is hereafter described.

A recombinant vector to be introduced into a plant can be prepared by cleaving with an appropriate restriction enzyme DNA comprising the promoter of the present invention and a structural gene and/or regulatory gene for enhancing stress tolerance, ligating an appropriate linker to the resulting DNA if necessary, and inserting the DNA into a cloning vector for the plant cell host. A binary vector type plasmid such as pBI2113Not, pBI2113, pBI101, pBI121, pGA482, pGAH, or pBIG, or an intermediate vector type plasmid such as pLGV23Neo, pNCAT, or pMON200, may be used as cloning vectors.

When a binary vector type plasmid is used, the gene of interest is inserted between the border sequences (LB, RB) of the binary vector. The resulting recombinant vector is amplified in *E. coli*. The amplified recombinant vector is then introduced into *Agrobacterium tumefaciens* C58, LBA4404, EHA101, C58C1Rif$^R$, EHA105, etc., by freeze-thawing, electroporation, or the like. The resulting *Agrobacterium* is used to transform the plant.

In the present invention, the three-member conjugation method (Nucleic Acids Research, 12:8711, 1984) may also be used in addition to the method described above to prepare an *Agrobacterium* to be introduced into plants. Specifically, plasmid-containing *E. coli* comprising the gene of interest, helper plasmid-containing *E. coli* (e.g. pRK2013), and an *Agrobacterium* are mixed and cultured on a medium containing rifampicin and kanamycin. Thus, a zygote *Agrobacterium* to be allowed to infect plants can be obtained.

For the expression of a foreign gene, etc., in plant bodies, a terminator for plants, etc., should be located downstream of the structural gene. Specific examples of terminator sequences that may be utilized in the present invention include cauliflower mosaic virus-derived and nopaline synthase gene-derived terminators. Terminators are not limited to the aforementioned, as long as they are known to be functional in plant bodies.

In order to efficiently select transgenic cells of interest, use of an effective selection marker gene is preferable. As such a selection marker, one or more genes selected from the kanamycin tolerance (NPTII) gene, the hygromycin phosphotransferase (htp) gene that confers tolerance to the antibiotic hygromycin on plants, the phosphinothricin acetyl transferase (bar) gene that confers tolerance on bialaphos, and the like, can be used. The promoter of the present invention and the selection marker gene may be incorporated together into a single vector. Alternatively, they may each be incorporated into separate vectors.

If the plant is infected with the thus prepared *Agrobacterium*, a transgenic plant of interest can be produced.

The transgenic plant is sowed onto a medium containing an adequate antibiotic, and plants containing promoters and genes of interest are selected. The selected plants are transferred to pots containing Bonsol No. 1, black soil, or the like and are further grown. Generally, the genes are introduced into the genome of the host plant in a similar manner. Due to differences in the locations on the genome into which the genes have been introduced, however, the expression of the introduced genes varies. This phenomenon is called a "position effect." By analyzing transgenic plants with DNA fragments from the introduced gene as a probe by Northern blotting, it is possible to select those transgenic plants in which the introduced gene is expressed more highly.

(2) Confirmation of Stress Tolerance

Whether or not the promoter of the present invention, or a structural gene and/or regulatory gene for enhancing stress tolerance, is integrated in the transgenic plant and in the subsequent generation thereof can be confirmed by extracting DNA from cells and tissues of those plants and detecting the introduced gene by PCR or Southern analysis, which are conventional in the art.

The expression level and the expression organ of a gene in a transgenic plant can be analyzed by extracting RNA from cells and tissues of the plant and detecting the mRNA of the introduced gene by RT-PCR or Northern analysis, which are conventional in the art. Alternatively, the transcription product of the introduced gene can be analyzed directly by Western blotting using an antibody against the above product or the like.

The tolerance to environmental stresses of the transgenic plant into which the promoter of the present invention has been introduced can be evaluated by setting the transgenic plant in a pot containing a soil comprising vermiculite, perlite, Bonsol, and the like or hydroponically growing plants, exposing the plants to various types of environmental stresses, and examining the survival of the plants. Environmental stresses include low temperature, dehydration, and salt stresses. For example, tolerance to dehydration stress can be evaluated by leaving the plant without water for 2 to 4 weeks and then examining the survival thereof. Tolerance to low temperature and freezing stresses can be evaluated by leaving the plant at 15 to −10° C. for 1 to 10 days, growing it at 20 to 35° C. for 2 days to 3 weeks, and then examining its survival ratio. Tolerance to salt stress can be evaluated by leaving the plant in 100 to 600 mM NaCl for 1 hour to 7 days, growing it at 20 to 35° C. for 1 to 3 weeks, and then examining its survival ratio. Thus, use of the promoter of the present invention can significantly enhance stress tolerance without retarding the growth of plants (particularly monocotyledonous plants).

(3) An Example of a Preferable Transgenic Plant

An example of a preferable transgenic plant according to the present invention is one prepared by introducing a vector comprising the functional OsDREB gene ligated downstream of the LIP9 or WSI724 promoter in a monocotyledonous plant, such as rice or wheat. Since the LIP9 promoter comprises 2 DRE regions, the OsDREB gene can effectively exhibit the effects of stress tolerance by binding to the cis elements. Similarly, the WSI724 promoter comprises 2 DRE regions, and thus, the expression level of the OsDREB gene can be enhanced and the stress tolerance of the plant can be improved.

EXAMPLES

The present invention is described in greater detail with reference to the following examples, although the technical scope of the present invention is not limited thereto.

Example 1

Identification of Stress-Inducible Rice Gene

Stress-inducible rice genes were searched for using cDNA microarrays and Northern analysis.

1. Production of Rice cDNA Microarray

Rice seeds (Nihonbare) that were grown hydroponically for 2 to 3 weeks were subjected to dehydration, salt, or low temperature stress. Dehydration stress was applied by air-drying at room temperature, salt stress was applied by culturing in a 250 mM NaCl solution, and low temperature stress was applied by cultivation at 4° C. The rice that had been subjected to each type of stress was frozen with liquid nitrogen. Total RNA was extracted from the frozen sample by the guanidine thiocyanate and cesium chloride method, and mRNA was prepared using the Oligo(dt)-cellulose column. cDNA was synthesized using the resulting mRNA as a template and using a HybriZAP-2.1 two-hybrid cDNA Gigapack cloning kit (Stratagene), and the cDNA was inserted and cloned at the EcoRI-XhoI cleavage site of HybriZAP-2.1 phagemid vector. This phagemid DNA was packaged using Gigapack III Gold packaging extract (Stratagene). The obtained lambda phage particles containing cDNA were used to infect host *E. coli*, which were then amplified, and these particles were subsequently recovered in the form of a phage suspension.

The nucleotide sequences of the cDNA clones were sequenced to select about 1,500 independent clones. The selected clones were amplified by PCR and stamped onto a poly-L-lysine-coated microslide glass (model S7444, Matsunami) using the GTMASS System (Nippon Laser and Electronic Laboratory). Thereafter, the clones were immobilized by UV cross-linking to produce the rice cDNA microarray (The Plant Cell, 2001, 13: 61-72 Seki et al.).

2. Microarray Analysis mRNAs were purified from rice plants that had been subjected to dehydration, salt, or low temperature stress or treated with 100 μM abscisic acid (5 hours or 10 hours) in the same manner as in the section above and from rice plants that had not been subjected to stress (without treatment). mRNA derived from rice plants without treatment was employed as a control, and mRNA derived from rice plants that had been subjected to each type of stress or treated with abscisic acid was employed as a sample. cDNA microarray analysis was carried out by dual-fluorescent labeling using Cy3 and Cy5. As a result of the microarray analysis, the genes with intensities of 1,000 or higher and the genes with expression levels as high as 3 times that of the control, were selected as candidate stress-inducible genes. Thus, a0022 (LIP9: SEQ ID NO: 2) and a0066 (WSI724: SEQ ID NO: 8) were selected as stress-inducible genes.

3. Expression Analysis Via Northern Hybridization

The characteristic expression of the genes selected in the section above was analyzed via Northern hybridization. Rice plants were first exposed to abscisic acid, dehydration, low temperature, salt, or water stress, and sampling was accomplished regarding the rice that had been subjected to stress every 0, 1, 2, 5, and 10 hours. The abscisic acid, dehydration, low temperature, or salt stress was applied in the same manner as in 1., and water stress was applied by immersing the plants in pure water. Total RNA was prepared from each sample, electrophoresis was carried out, and the expression of each gene was observed by the Northern method. The results are shown in FIG. 1.

As is apparent from FIG. 1, the expression of the a0022 gene was induced by the abscisic acid, dehydration, low temperature, or salt stress. In particular, the expression thereof was rapidly induced by abscisic acid, dehydration, or salt stress. In contrast, the expression thereof was slowly induced by low temperature stress. The a0066 gene was a target of OsDREB, based on the expression pattern when stress is applied (the expression pattern is inducible by dehydration, salt, and low temperature stresses and the rate of induction by low temperature is slower than that by dehydration and salt).

Example 2

Screening of Promoter Sequence

1. Screening of Rice Genome Database

Using BLAST, the rice genome database of DDBJ was searched for a identical site of cDNA:a0022 (LIP9: SEQ ID NO: 2), which was selected as a stress-inducible gene in Example 1. As a result, in the gene in which identity was observed, the sequence located 1.1 kb upstream of the initiation codon toward the 5' side of the gene was selected as a promoter sequence (SEQ ID NO: 1). A similar search was conducted concerning a0066 (WSI724: SEQ ID NO: 8), and the promoter sequence thereof (SEQ ID NO: 10) was selected.

FIG. 2 shows the structure of the LIP9 promoter region. As is apparent from FIG. 2, LIP9 comprises in its structure 2 DRE cis elements ((A/G)CCGAC). FIG. 7 shows the structure of the WSI724 promoter region. The WSI724 promoter was also found to comprise in its structure 2 DRE cis elements ((A/G)CCGAC).

2. Cloning

Based on the selected promoter sequences, primers were designed, PCR was carried out using rice genome DNA as a template, and cloning was carried out. The primer sequences and the conditions for PCR used are as follows. Primer sequences for LIP9 promoter:

```
                                            (SEQ ID NO: 3)
Forward primer: 5'-CACGAAGCTTTCATCAGCTATTCATCAA-3'

(SEQ ID NO: 4)
Reverse primer: 5'-CCGGATCCTCGATCGATGGATTCAGCTA-3'
```

Primer sequences for WSI724 promoter:

```
                                           (SEQ ID NO: 11)
Forward primer: 5'-CCATTGGATCCAGCCGTGGAAGTCCAAC-3'

(SEQ ID NO: 12)
Reverse primer: 5'-GCCGGGGATCCTTGGCGCCTCTCTCTCT-3'
```

PCR conditions: 30 cycles of 95° C. for 1 minute, 55° C. for 1 minute, and 68° C. for 2 minutes Example 3

Activity of LIP9 Promoter Against Stress (1) Preparation of Transgenic Plant

Figure 3:
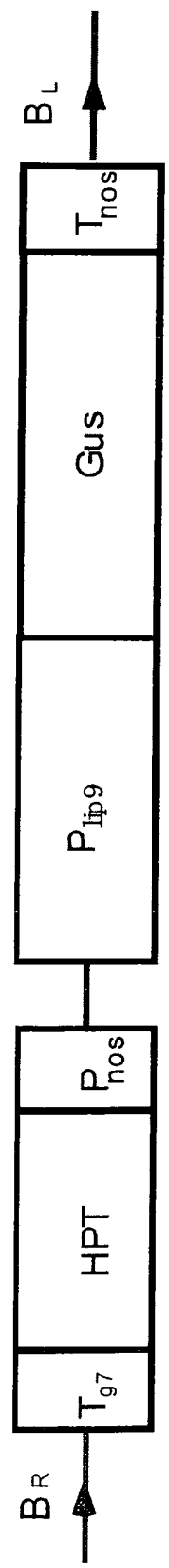
FIG. 3 shows the structure of a GUS expressing construct, wherein $T_{g7}$ represents a g7 terminator, HPT represents hygromycin phosphotransferase, $P_{nos}$ represents an Nos promoter, and $T_{nos}$ represents a Nos terminator.

The promoter site of pBIG29APHSNot was substituted with an ubiquitin promoter of maize to produce G-ubi plasmid. The G-ubi plasmid was cleaved with BamHI-HindIII and ligated to a fragment of a similarly cleaved LIP9 promoter. The plasmid into which the LIP9 promoter had been incorporated was cleaved with BamHI-EcoRI and ligated to the Gus gene, which was similarly cleaved out from pBI221 (Clontech) with BamHI-EcoRI, to produce a GUS-expressing construct G-LIP9:GUS (FIG. 3). The plasmid G-LIP9:GUS was introduced by electroporation into Agrobacterium EHA105, which was washed with 10% glycerol after culturing, thereby preparing Agrobacterium EHA105 (G-LIP9:GUS). Rice was infected with this Agrobacterium EHA105 (G-LIP9:GUS) in the following manner to prepare a transgenic plant of interest.

Rice seeds were immersed in 70% ethanol for 1 minute and sterilized by immersion in 2% sodium hypochlorite for 1 hour. The sterilized seeds were then washed with sterilized water, and 9 grains each of the seeds were sowed onto a plate of N6D solid medium (3.98 g of CHU[$N_6$] Basal Salt Mixture (Sigma), 30 g of sucrose, 100 mg of myo-inositol, 300 mg of casamino acid, 2,878 mg of L-proline, 2 mg of glycine, 0.5 mg of nicotinic acid, 0.5 mg of pyridoxine hydrochloride, 1 mg of thiamine hydrochloride, 2 mg of 2,4-D, and 4 g of Gellite per liter; pH 5.8), followed by culturing for 24 days. Thus, callus formation was induced. The callus formed from approximately 20 grains of the seeds was transferred to new N6D solid medium, followed by culturing for an additional three days.

Separately, Agrobacterium EHA105 (G-LIP9:GUS) was cultured in 5 ml of YEP medium containing 100 mg/l rifampicilin and 20 mg/l kanamycin (10 g of Bacto peptone, 10 g of Bacto yeast extract, 5 g of NaCl, and 406 mg of $MgCl_2.6H_2O$ per liter; pH 7.2) at 28° C. for 24 hours. This Agrobacterium was diluted with AAM medium containing 20 mg/l acetosyringon (10 mg of $MnSO_4.5H_2O$, 3 mg of $H_3BO_3$, 2 mg of $ZnSO_4.7H_2O$, 250 μg of $Na_2MoO_4.2H_2O$, 25 μg of $CuSO_4.5H_2O$, 25 μg of $CoCl_2.6H_2O$, 750 μg of KI, 150 mg of $CaCl_2.2H_2O$, 250 mg of $MgSO_4.7H_2O$, 40 mg of Fe-EDTA, 150 mg of $NaH_2PO_4.2H_2O$, 1 mg of nicotinic acid, 10 mg of thiamine hydrochloride, 1 mg of pyridoxine hydrochloride, 100 mg of myo-inositol, 176.7 mg of L-arginine, 7.5 mg of glycine, 900 mg of L-glutamine, 300 mg of aspartic acid, and 3 g of KCl per liter; pH 5.2) to bring $O.D._{660}$ to 0.1. Thus, 20 ml of Agrobacterium suspension was prepared.

Subsequently, the Agrobacterium suspension was added to and then mixed with the callus, which was cultured for 3 days, for 1 minute. Thereafter, this callus was placed on a sterilized paper towel to remove excess Agrobacterium suspension and then cultured on 2N6-AS solid medium, on which the sterilized filter paper was placed, (3.98 g of CHU[$N_6$] Basal Salt Mixture, 30 g of sucrose, 10 g of glucose, 100 mg of myo-inositol, 300 mg of casamino acid, 2 mg of glycine, 0.5 mg of nicotinic acid, 0.5 mg of pyridoxine hydrochloride, 1 mg of thiamine hydrochloride, 2 mg of 2,4-D, 10 mg of acetosyringon, and 4 g of Gellite per liter; pH 5.2) at 25° C. for 3 days in the dark. After culturing for 3 days, the culture product was thoroughly washed with an aqueous solution of 3% sucrose containing 500 mg/l carbenicillin until the solution did not become clouded. The washed culture product was further cultured on N6D solid medium containing 500 mg/l carbenicillin and 10 mg/l hygromycin for 1 week. Thereafter, the resulting culture product was transferred onto a N6D solid medium containing 500 mg/l carbenicillin and 50 mg/l hygromycin and cultured for 18 days. Furthermore, the callus was transferred to a redifferentiation medium (4.6 g of Murashige and Skoog Plant Salt Mixture (Nihon Pharmaceutical Co., Ltd), 30 g of sucrose, 30 g of sorbitol, 2 g of casamino acid, 100 mg of myo-inositol, 2 mg of glycine, 0.5 mg of nicotinic acid, 0.5 mg of pyridoxine hydrochloride, 0.1 mg of thiamine hydrochloride, 0.2 mg of NAA, 2 mg of kinetin, 250 mg of carbenicillin, 50 mg of hygromycin, and 8 g of agarose per liter; pH 5.8). The product was transferred to a new medium every week and redifferentiated. Those having buds that had grown to approximately 1 cm were transferred to a hormone-free medium (4.6 g of Murashige and Skoog Plant Salt Mixture (Nihon Pharmaceutical Co., Ltd), 30 g of sucrose, 2 mg of glycine, 0.5 mg of nicotinic acid, 0.5 mg of pyridoxine hydrochloride, 0.1 mg of thiamine hydrochloride, 50 mg of hygromycin, and 2.5 g of Gellite per liter; pH 5.8). Plant bodies, which have grown to approximately 8 cm on the hormone-free medium, were transferred to a pot containing synthetic particulate potting soil (Bonsol No. 1, Sumitomo Chemical Co., Ltd.) to allow the transgenic plants to produce seeds.

Similarly, the rd29A promoter (Nature Biotechnology, 1999, 17: 287-291), the 35S promoter, or the salT promoter (SEQ ID NO: 5) was ligated upstream of the GUS gene to produce constructs. The obtained constructs were introduced into rice and/or tobacco.

The salT promoter is a stress-inducible promoter isolated from the rice genome via screening conducted in the same manner as with the case of the LIP9 promoter. The ID No. of cDNA of the salT promoter immobilized on the microarray is a2660. Although the salT promoter does not comprise a special cis sequence in its structure, it is confirmed that expression thereof is induced by the abscisic acid, dehydration, low temperature, or salt stress (Japanese Patent Application No. 2002-377316).

(2) Promoter Activity Against Dehydration Stress

The $T_2$ generation of the obtained GUS-expressing transgenic rice was grown hydroponically for 2 weeks and exposed to dehydration stress in the same manner as in Example 1.

In the case of GUS-expressing transgenic tobacco, a plant, which was regenerated from a $T_1$ generation plant, was grown in a plant cone for 3 to 5 weeks, and a grown leaf was bisected. One part thereof was designated as a control, and the other was exposed to dehydration stress by being air dried at room temperature.

Figure 4:
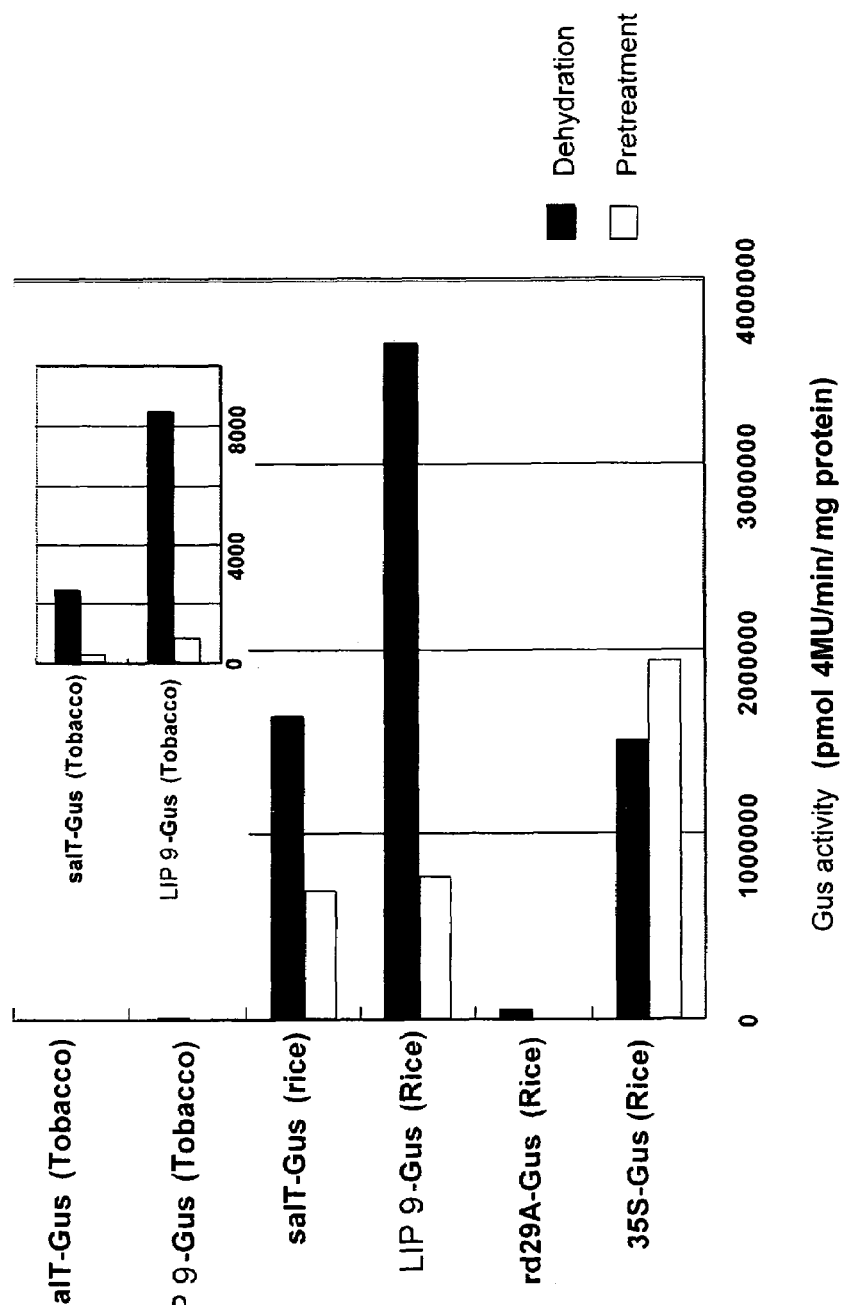
FIG. 4 is a graph showing the GUS activities of transgenic tobacco or rice prepared by introducing various promoters ligated to GUS genes when dehydration stress is applied.

The GUS activities of both transgenic rice and tobacco were assayed based on changes in fluorescence intensities resulting from the decomposition of 4-methylumbelliferyl-β-D-glucuronide. FIG. 4 shows the GUS activities of the transgenic plants to which various promoters were introduced at the time of the application of dehydration stress.

As is apparent from FIG. 4, the activity level of the stress-inducible salT or LIP9 promoter in monocotyledonous plants, i.e., rice, is higher than that of the rd29A promoter. In particular, the activity of the LIP9 promoter was as high as approximately two times that of the salT promoter. While the LIP9 promoter also exhibited stress-inducible promoter activities in tobacco, which is a dicotyledonous plant, its activity was weaker than that in rice.

(3) Promoter Activity Against Salt Stress

Subsequently, the entire body of the rice to which the LIP9 promoter-GUS construct has been introduced was immersed in salt water and then subjected to GUS staining. As a result, the entire plant was stained (FIG. 5). Based on this, the LIP9 promoter was found to function in all parts of the plant that had been subjected to salt stress.

Example 4

WSI724 Promoter Activity Against Stress

In the same manner as in Example 3, transgenic rice was produced using the WSI724 promoter, and stress response thereof was examined.

(1) Production of Transgenic Plants

The promoter site of pBIG29APHSNot was substituted with an ubiquitin promoter of maize to produce G-ubi plasmid. The G-ubi plasmid was cleaved with BamHI-HindIII and ligated to a fragment of the similarly cleaved WSI724 promoter. PCR fragment of the WSI724 promoter were cut with BamHI and blunt-ended, and ligated to a site of the pBIG vector, which was cleaved with SmaI to produce a GUS-expressing construct (WSI724:GUS). Subsequently, WSI724:GUS plasmid was introduced by electroporation into *Agrobacterium* EHA105, which was washed with 10% glycerol after culturing, thereby preparing *Agrobacterium* EHA105 (WSI724:GUS). Rice was infected with this *Agrobacterium* EHA105 (WSI724:GUS) to prepare a transgenic plant of interest.

(2) Promoter Activity Against Dehydration Stress

The GUS-expressing transgenic rice was exposed to dehydration stress in the same manner as in Example 3 to assay GUS activities thereof based on changes in fluorescence intensities resulting from the decomposition of 4-methyltimbelliferyl-β-D-glucuronide. As a result, GUS activities observed in the leaves of the transgenic rice to which dehydration stress had been applied (where the leaves had been cut and allowed to stand for 24 hours) were higher than those observed in the leaves of the controls (where such leaves had been cut and then frozen immediately). The transgenic rice to which dehydration stress had been applied (for 24 hours) was subjected to GUS staining, and GUS activities were observed both in the roots and in the leaves.

Example 5

Expression of Genes Introduced into Transgenic Rice, LIP9 Genes, and WSI724 Genes A transgenic plant was prepared in the same manner as in Example 3. This transgenic plant was prepared by introducing the OsDREB1A gene (SEQ ID NO: 6) or the DREB1C gene (SEQ ID NO: 8) that is under the control of an ubiquitin promoter of maize or 35S promoter into rice. The mRNA level of the OsDREB1A and DREB1C genes that had been introduced into the transgenic plant and the mRNA level of the LIP9 (a0022), WSI724 (a0066), and salT (a2660), the expression of which was considered to be altered by the introduced genes, were analyzed by the Northern method.

The OsDREB1A gene (SEQ ID NO: 6), the DREB1C gene (SEQ ID NO: 7), the LIP9 gene (a0022, SEQ ID NO: 2), the WSI724 gene (a0066, SEQ ID NO: 8), and the salT gene (a2660, SEQ ID NO: 9) were employed as probes (the sequences of the coding regions were employed as probes concerning SEQ ID NOs: 6 and 7 in the sequence listings). As a control, rice in which only the vector had been transformed was similarly analyzed.

Figure 6:
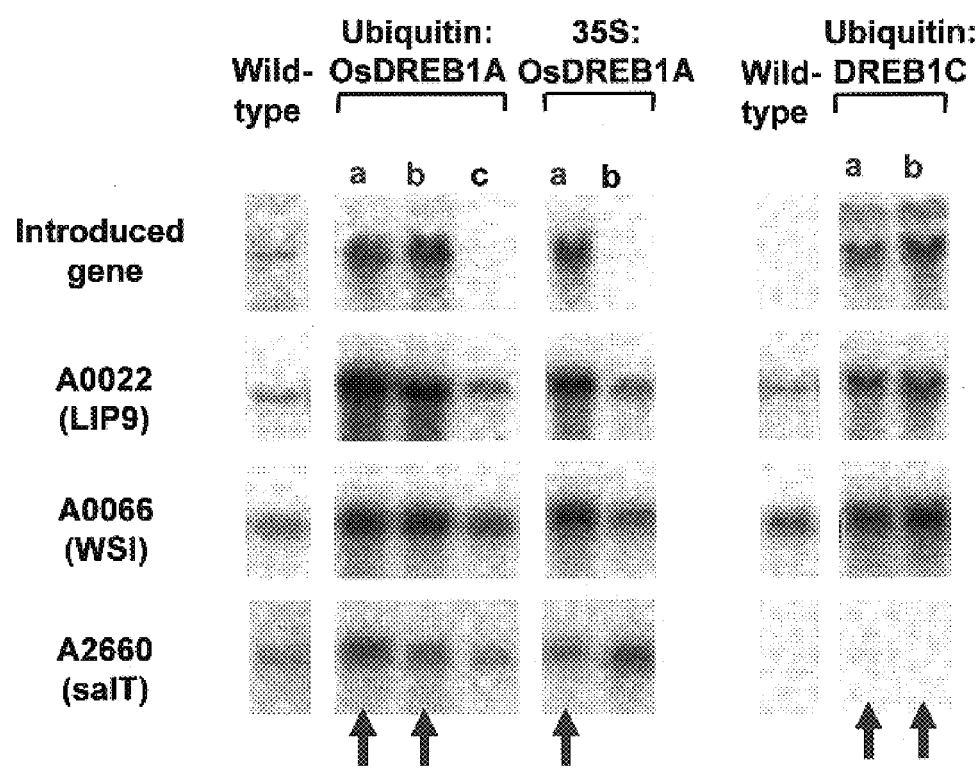
FIG. 6 shows the results of analyzing the expression levels of the introduced genes and the target genes (LIP9 (a0022), WSI724 (a0066), and salT (a2660)) in the transgenic rice and in the wild-type rice by the Northern method, wherein "a," "b," and "c" each independently represent a transgenic plant line.
Figure 8:
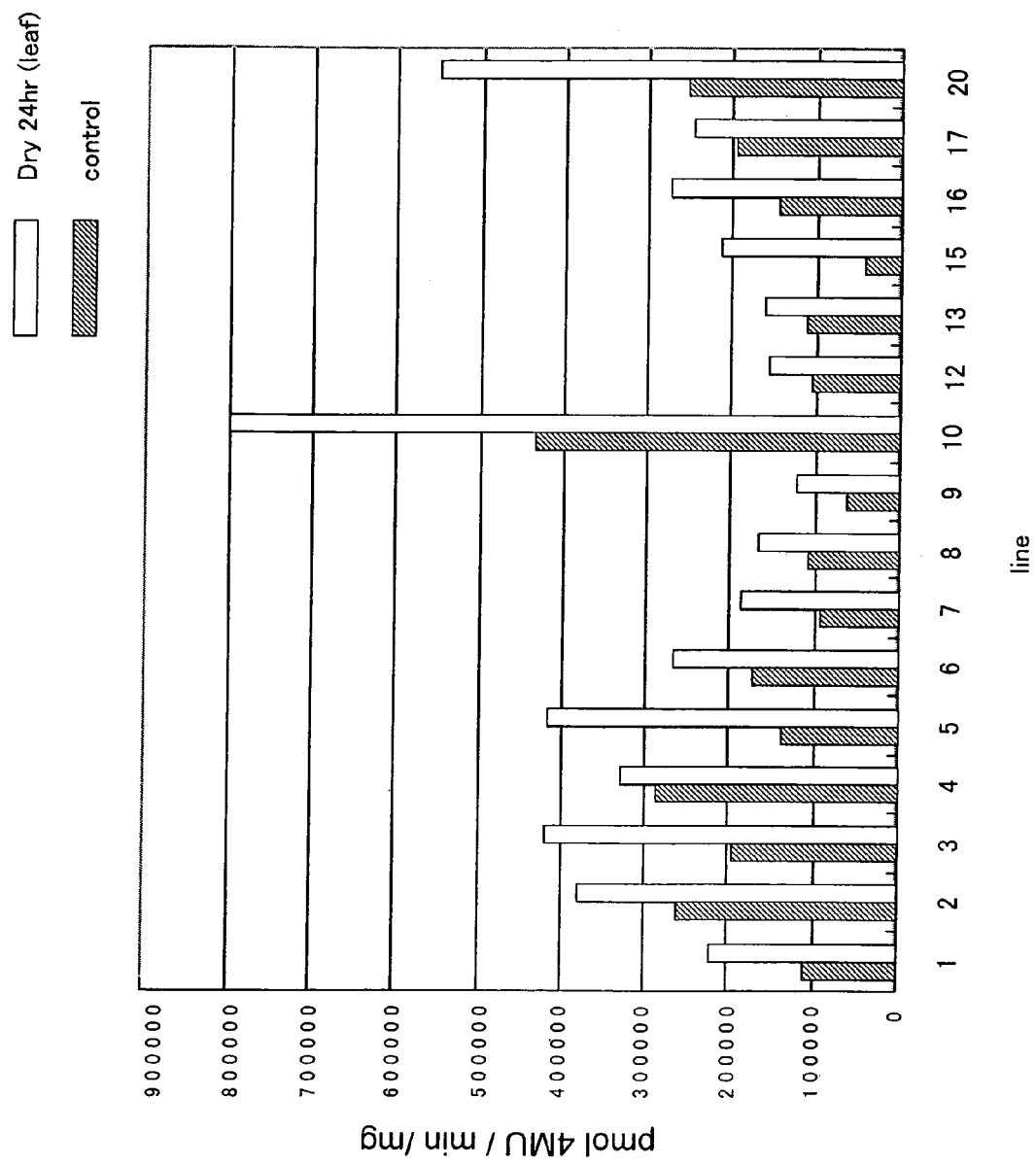
FIG. 8 is a graph showing the GUS activities of transgenic rice prepared by introducing a WSI724 promoter ligated to GUS genes when dehydration stress is applied, wherein right bars represent GUS activities when dehydration stress is applied and left bars represent the controls.
Figure 9:
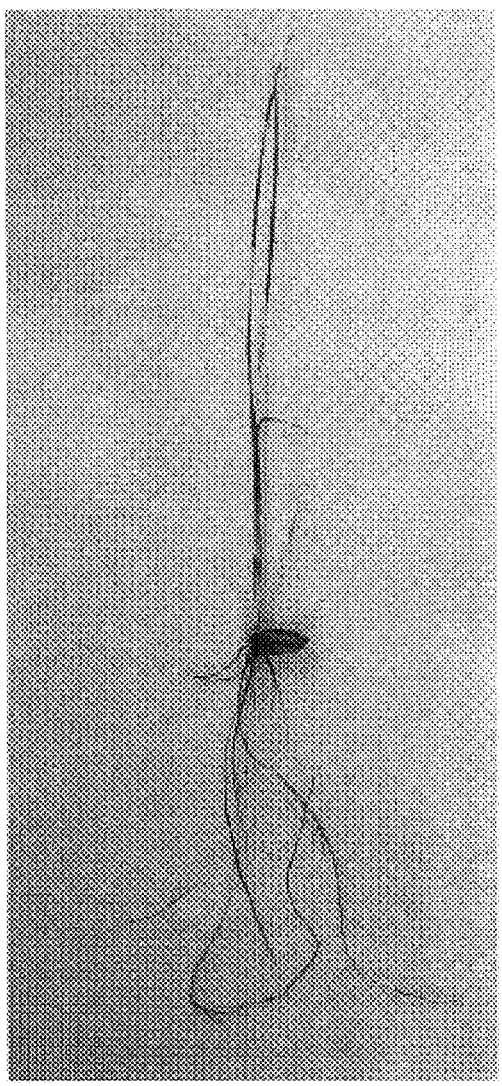
FIG. 9 is a photograph showing the results of GUS staining on transgenic rice prepared by introducing a WSI724 promoter ligated to GUS genes when dehydration stress is applied.

The transgenic rice was selected in a 0.1% Benlate solution containing 30 mg/ml hygromycin for 5 days. Thereafter, the plant was transferred to a pot containing Bonsol No. 1 and was grown for 12 days. The wild-type rice was grown similarly. Total RNA was extracted from each plant and electrophoresed. Expression of each gene was analyzed by the Northern method in the same manner as in Example 1. The results are shown in FIG. 6, wherein "a," "b," and "c" each independently represent a transgenic plant line.

In the transgenic rice into which the OsDREB1A and DREB1C genes had been introduced, the expression of the LIP9 gene having the DRE sequence in the promoter region was found to be induced. In contrast, the expression of the salT gene having no DRE sequence in the promoter region was found to be inconsistent with the expression of the introduced gene (OsDREB1A or DREB1C). Also, the expression of the WSI724 gene, which comprises the DRE sequence in the promoter region and is deduced to be a target of OsDREB, as with the LIP9 was induced by these transgenic plants.

The LIP9 or WSI724 promoter comprises the DRE sequence, and the expression level of the LIP9 or WSI724 gene is high in transgenic plants wherein overexpression of the OsDREB1A genes is observed. LIP9 and WSI724 was considered to be the target gene of the OsDREB genes, including OsDREB1A. Accordingly, the LIP9 or WSI724 promoter was deduced to be optimal for overexpression of the OsDREB gene.

Reference Example 1

Production of pBE35S:OsDREB1A, G-ubi:OsDREB1A, and G35S- ShΔ:OsDREB1A

G-ubi and G35S-ShΔ were prepared as follows. At the outset, pBIG plasmid (Nucleic Acids Research 18: 203, 1990) was cleaved with BamHI, blunt-ended, and ligated to delete the BamHI cleavage site. Thereafter, the plasmid was cleaved with HindIII and EcoRI. The resulting fragment was ligated to a fragment of approximately 1.2 kb, which was obtained by cleavage of pBE2113Not plasmid in the same manner, thereby preparing a pBIG2113Not plasmid.

Subsequently, pBIG2113Not was cleaved with HindIII and BamHI and ligated to a fragment of rd29A promoter (approximately 0.9 kb, Nature Biotechnology 17: 287-291, 1999), which was cleaved in the same manner, thereby preparing pBIG29APHSNot plasmid. Further, this pBIG29APHSNot plasmid was cleaved with HindIII and SalI and then ligated to a fragment of the ubiquitin gene (Ubi-1) promoter (approximately 2.0 kb, Plant Molecular Biology 18: 675-689, 1992) of maize or a fragment (approximately 1.6 kb, Proceeding National Academy of Science USA 96: 15348-15353, 1999) containing CaMV 35S promoter of p35S-shΔ-stop and a part of the intron of a sucrose synthase gene (Sh1) of maize, which was cleaved in the same manner. Thus, G-ubi plasmid or G35S-shΔ plasmid was prepared.

pBE2113Not, G-ubi, and G35S-shΔ described above were each cleaved with BamHI, and ligated to a fragment of the similarly cleaved OsDREB1A gene encoding a transcription factor of rice using Ligation High (Toyobo Co., Ltd.). *E. coli* DH5α was transformed using the thus obtained ligation product. After the transgenic *E. coli* was cultured, pBE35S: OsDREB1A, G-ubi: OsDREB1A, and G35S-ShΔ: OsDREB1A plasmids were purified therefrom. Subsequently, the nucleotide sequences thereof were determined, and those having the OsDREB1A gene bound in the sense direction were selected.

The plasmid pBE35S: OsDREB1A-containing *E. coli* DH5α, helper plasmid pRK2013-containing *E. coli* HB101, and *Agrobacterium* C58 were mixed and cultured on LB agar medium at 28° C. for 24 hours. Generated colonies were scraped off and suspended in 1 ml of LB medium. This suspension (10 μl) was applied to LB agar medium containing 100 mg/l rifampicilin and 20 mg/l kanamycin and cultured at 28° C. for 2 days, thereby obtaining zygote *Agrobacterium* C58 (pBE35S: OsDREB1A). By electroporation, the G-ubi: OsDREB1A plasmid and the G35S-ShΔ: OsDREB1A plasmid were separately introduced into *Agrobacterium* EHA105, and washed with 10% glycerol after culturing. Thus, *Agrobacterium* EHA105 (G-ubi: OsDREB1A) and *Agrobacterium* EHA105 (G35S-shΔ: OsDREB1A) were obtained.

All publications, patents, and patent applications cited herein are incorporated herein by reference in their entirety.

INDUSTRIAL APPLICABILITY

The present invention provides a stress-inducible promoter that is effectively functional in monocotyledonous plants. Such promoter comprises the DRE sequence. If the OsDREB gene or the like is ligated so as to be under the control of the promoter and introduced into plants, accordingly, transgenic monocotyledonous plants, such as rice, having potent stress tolerance can be produced.

Free Text of Sequence Listing
  SEQ ID NO: 3—description of artificial sequence: primer
  SEQ ID NO: 4—description of artificial sequence: primer
  SEQ ID NO: 11—description of artificial sequence: primer
  SEQ ID NO: 12—description of artificial sequence: primer

What is claimed is:

1. An isolated rice promoter consisting of DNA that consists of the nucleotide sequence as shown in SEQ ID NO: 1, wherein said promoter is a stress-inducible promoter.

2. The promoter according to claim 1, wherein the stress is dehydration stress, low temperature stress, or salt stress.

3. A recombinant vector comprising the promoter according to claim 1.

4. The vector according to claim 3, further comprising structural coding sequences and/or regulatory gene coding sequences for enhancing stress tolerance which are contained so as to be functional under the control of the promoter.

5. The vector according to claim 4, wherein the structural and/or regulatory gene coding sequences for enhancing stress tolerance are selected from the group consisting of the P5CS (delta-1-pyrroline-5-carboxylate synthase) gene, the AtGolS3 (*Arabidopsis thaliana* galactinol synthase3) gene, the *Arabidopsis thaliana*-derived DREB (dehydration responsive element binding protein) transcription factor gene, the rice OsOREB (Oryza sativa dehydration responsive element binding protein) transcription factor gene, and the NCED (9-cis-epoxycarotenoid dioxygenase) gene.

6. The vector according to claim 5, wherein the structural and/or regulatory gene coding sequences for enhancing stress tolerance is the rice OsDREB transcription factor gene.

7. A method for enhancing stress tolerance of a plant, said method comprises: introducing the vector according to claim 4 into the plant, and expressing the gene coding sequences, wherein expression of said coding sequences enhances stress tolerance in the plant as compared to an untransformed plant of the same species.

8. A recombinant vector comprising the promoter according to claim 2.

9. The vector according to claim 8, further comprising structural and/or regulatory gene coding sequences for enhancing stress tolerance which are contained so as to be functional under the control of the promoter.

10. A method for enhancing stress tolerance of a plant, said method comprises: introducing the vector according to claim 5 into the plant, and expressing the gene coding sequences, wherein expression of said coding seguences enhances stress tolerance in the plant as compared to an untransformed plant of the same species.

11. The method of claim 7, wherein the plant is a monocotyledonous plant.

12. The method of claim 10, wherein the plant is a monocotyledonous plant.

\* \* \* \* \*

SEQUENCE LISTING

```
<160> NUMBER OF SEQ ID NOS: 12

<210> SEQ ID NO 1
<211> LENGTH: 1066
<212> TYPE: DNA
<213> ORGANISM: Oryza sativa
<220> FEATURE:
<223> OTHER INFORMATION: Inventor: Shinozaki, Kazuko; Katsura, Koji;
      Ito, Yusuke

<400> SEQUENCE: 1
tcatcagcta tcatcaaagc gaaggaaaga aagaaaaata aaaggaaaag aactggctgg      60
aaattagaga agccccggac gactcgatct gggggtggca aattaatcag tgtgatcaac     120
agggataact tatcccgtcc gaccaaatcc accaaccaaa ccaagacccg atttgttagg     180
ctgtgaaaga cggatcagtg ggaccctgat ctacggaccc catatgtcac cgtccaggtc     240
tctggatctc tcccgtcgtc ctaatcagac accgcgcgcg cggtgccgtc gctctcgagc     300
cgtgtcccgc tcccaactcg tcacaaaagc gatcacagac tcttccttcc tctgctggga     360
gagaagaaaa attggccgcg atgatgccga taaagaggaa aaagggatga gaatccgatg     420
gaaaaaaact gatgttaatc tatcgctact gctgcgcact aagacgaatc gtatccgaac     480
aagaaacgct tacgttactg ttcctaaatg gatcgctccg ctcatcactt aaccaaaaat     540
cgattaggaa attgacggac agcgacgccc gaagccaagt gtctcgtcgc gtaggcgtcg     600
aggcctcgaa gcagagggag cggagaggcg gacgcgccgc ccacgcctcc tctccctcgg     660
tgacacggcc gtctggctcc acatggcgcc gacctctccc gatgcgtcca cccgtcccga     720
ggcaccgcca cgtcggaacc agccggccgc cccacgcgat tgccgacacg cgtcgcggcg     780
ccactggctc acccgctgcc tgcctctgcc tgcccccat ctcgtcgcca tttcccgccc     840
acgcttcttg tcctcgcgtc gcctacgcgt acgtacgata caaacgccgc acctttcgat     900
cccctccgct atataaggag ggcatctgcc tcgccacctt cttcatccga aagcaaaagc     960
gactcgtcac agctcaaaca agtcaagagc gaatagttct tgctgatctg ttgtttgatt    1020
```

```
actttagttc tcgagaggct ttagctgaat ccatcgatcg aggatg                    1066

<210> SEQ ID NO 2
<211> LENGTH: 1245
<212> TYPE: DNA
<213> ORGANISM: Oryza sativa

<400> SEQUENCE: 2
gctagcagag ctcgtcacag ctcaaacaag tcaagagcga atagttcttg ctgatctgtt      60
gtttgattac tttagttctc gagaggcttt agctgaatcc atcgatcgat catggaggat     120
gagaggaaca cggagagcca ccagggtggc gaggctgcag agcaggtgga ggtgaaggac     180
aggggcctct tcgacaacct ccttggcagg aagaaggacg atcagccgga ggagaagaag     240
catgaggagg agcttgtcac cggcatggag aaggtctccg tggaagagcc aaagaaggag     300
gagcaccacg ccgagggcga gaagaaggag agcctcctct ccaagctgca ccgatccagc     360
tccagctcca gctcgtcgag tgatgaggaa gaggaggtga tcgatgacaa cggcgaggtg     420
gtcaagagga agaagaagaa ggggctcaag gagaagatca aggagaagct gcccggccac     480
aaggaccatg ccggtgagca tgctcctccg cccgcggcga cgggcttccc gcgccggctc     540
cgctgcatcc gtggtgacgg ccgcgcccac gccactcctg ctcccgtggt gactcacggc     600
gatcaccacc acgacaccgc cgtccccgtg gaaaagatcg agggtgatca cgccagacgg     660
aggcgaccct gccacgtgca cccgaggagg aaaaaagggc ttcctcgaca agatcaagga     720
gaagctgccc ggcggccaca agaagccgga agacgcaact gctgtgccgc cgccggccgc     780
ctcaccggct gctcctgcca ctactccggc gccagcacac ccaccgccgg ctacagagga     840
agtgagcagc ccgatgggga aggagaagaa gggtatactg gcaagatca tggagaaact     900 gcccggttac acaagggct ccggcgagga agacaagacc gccgccgccg ccaccggcga     960
gcacaagagc agcgcttaat ggggcgtgt gtgagaccag gccatggttg gaatttggaa    1020
gtgtttggcg tgtgttagtt tggtgctttt tctgcactgc agctttgtta agttcgtgtc    1080
aagattggtc aaggcctggt cagcgaagcc cgatcagtga tcgaagtttg tgtttcgtgt    1140
ggggtacggg cttcagtttg ctatagtcaa gtactagatg ttgagtttgt ttaattatta    1200
ttggcactct tgtattggtt ttgggctggg cattctgcct tggta                    1245

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 3
cacgaagctt tcatcagcta ttcatcaa                                         28

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 4
ccggatcctc gatcgatgga ttcagcta                                         28

<210> SEQ ID NO 5
```

<211> LENGTH: 1608
<212> TYPE: DNA
<213> ORGANISM: Oryza sativa

<400> SEQUENCE: 5

| | | | | | |
|---|---|---|---|---|---|
| caacaaccac | tactgaacac | ggctaagtgt | gtttcctctc | ctcgaagatg | tcgttattgc | 60 |
| gttcttttct | gctattccat | acatatcaat | ctctagagga | acaccttact | ctagctttca | 120 |
| gacaagggac | ggtggtaaat | cacgtcgtat | cctccatggg | gtgtgctccg | aaaaaccttc | 180 |
| cctcatgcat | tagagatcat | gggtggaatt | tagcgatggc | acaccttatt | tataatttag | 240 |
| ttactctccg | gcgtaccat | ctgcttccgt | ttgttgatcg | atgctggcga | tgatgtgtgt | 300 |
| gagtatcgat | caacagaatg | atcggacgct | attttgggg | tcgttttttt | tcagcattga | 360 |
| ggagggatga | ggattgcttg | caacatgcag | gtgctgctca | aaacaacggt | taagcagata | 420 |
| tccgtcaatt | tgatagtaag | atctgtaacg | cgtggtcttt | cgagctgaaa | actatggact | 480 |
| ctttgaaaca | aagataatat | tatattaaat | tctattattc | aaagatatct | aaatatttag | 540 |
| aaagatatta | ataatgttat | taaactttga | cttacttaaa | acaagtccaa | aactgcatgt | 600 |
| ccctaaatcg | ccagaagata | aggaacacct | gtacccgtga | taacagaggg | gtatgaaatt | 660 |
| tggacacgag | gcttctttgg | cagacgtggc | gctgagtgag | cttggctcgc | ttggtcaaac | 720 |
| tccgtgcagg | gacattcagt | tagctagcta | gcagcattgt | cgacaataag | atagccttta | 780 |
| aatgttagca | ctcaccagct | tgtcaaaaac | caaggcttgg | tgacggcggc | ttcagaatga | 840 |
| aggatagatg | gataaatgtc | tagaatatta | taaagtccaa | caaagatgg | agcacatgca | 900 |
| tgaaagatta | cgtacacgaa | tgcagttgat | acagtggatg | ttaggcataa | gaagcactat | 960 |
| aaatagaggg | tgcaatcccc | attgccctac | acaactacac | aagtcgacta | tcattacaag | 1020 |
| gaaatttaag | cgaccacgaa | ggtatgaaag | catagcagta | ctctgcattt | ttttttttg | 1080 |
| atgttgttct | agctagctct | gcttaaggtt | ttcctttctt | tcgttctttg | ttttttttt | 1140 |
| gtaagctcaa | ctagttgcat | gcaatttaga | ttttatcctt | ttacagttgg | aaaaacatcc | 1200 |
| ctataaatat | taccatgaat | gcatagagat | tcgaggaagc | tacaaattgg | acgactgatt | 1260 |
| ccaaaaaaaa | aaaaaaaatc | agatggtcac | atcattgcta | ttgttttgtg | aaagtacaaa | 1320 |
| agcactcgtt | cggattcaaa | ttacttgtgc | aaattaatta | aaaccatag | aaatgatcat | 1380 |
| gttaccccta | cacatttcgg | aaacaatacc | atatatgtta | gtgtgcgatc | attcaaattg | 1440 |
| atttatatct | gaacaaaact | gagtgggaat | acggtgagca | aacttgacga | ttccaaaata | 1500 |
| atttatattt | aggcaaaatt | ttacaacttc | aaagttcaaa | caagctaacc | tgaaaaatca | 1560 |
| tgtttgaatt | tactaagatg | tgcttttgta | tttactaaac | agagtatg | | 1608 |

<210> SEQ ID NO 6
<211> LENGTH: 927
<212> TYPE: DNA
<213> ORGANISM: Oryza sativa
<220> FEATURE:
<221> NAME/KEY: CDS
<222> LOCATION: (69)..(782)

<400> SEQUENCE: 6
cacactcgag cagagcaaat acagttcagg aatcaggagc aagcagaaac acacacacaa      60 atccgaaag atg tgc ggg atc aag cag gag atg agc ggc gag tcg tcg ggg     110
         Met Cys Gly Ile Lys Gln Glu Met Ser Gly Glu Ser Ser Gly
           1               5                  10 tcg ccg tgc agc tcg gcg tcg gcg gag cgg cag cac cag acg gtg tgg      158
Ser Pro Cys Ser Ser Ala Ser Ala Glu Arg Gln His Gln Thr Val Trp

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| 15  |     |     |     |     | 20  |     |     |     |     | 25  |     |     |     |     | 30  |     |

```
acg gcg ccg ccg aag agg ccg gcg ggg cgg acc aag ttc agg gag acg    206
Thr Ala Pro Pro Lys Arg Pro Ala Gly Arg Thr Lys Phe Arg Glu Thr
                 35                  40                  45 agg cac ccg gtg ttc cgc ggc gtg cgg cgg agg ggc aat gcc ggg agg    254
Arg His Pro Val Phe Arg Gly Val Arg Arg Arg Gly Asn Ala Gly Arg
             50                  55                  60 tgg gtg tgc gag gtg cgg gtg ccc ggg cgg cgc ggc tgc agg ctc tgg    302
Trp Val Cys Glu Val Arg Val Pro Gly Arg Arg Gly Cys Arg Leu Trp
         65                  70                  75 ctc ggc acg ttc gac acc gcc gag ggc gcg gcg cgc gcg cac gac gcc    350
Leu Gly Thr Phe Asp Thr Ala Glu Gly Ala Ala Arg Ala His Asp Ala
     80                  85                  90 gcc atg ctc gcc atc aac gcc ggc ggc ggc ggc ggg gga gca tgc        398
Ala Met Leu Ala Ile Asn Ala Gly Gly Gly Gly Gly Gly Ala Cys
 95                 100                 105                 110 tgc ctc aac ttc gcc gac tcc gcg tgg ctc ctc gcc gtg ccg cgc tcc    446
Cys Leu Asn Phe Ala Asp Ser Ala Trp Leu Leu Ala Val Pro Arg Ser
                115                 120                 125 tac cgc acc ctt cgc cga cgt ccg cca cgc cgt gcc gag gcc gtc gag    494
Tyr Arg Thr Leu Arg Arg Arg Pro Pro Arg Arg Ala Glu Ala Val Glu
            130                 135                 140 gac ttc ttc cgg cgc cgc ctc gcc gac gac gcg ctg tcc gcc acg tcg    542
Asp Phe Phe Arg Arg Arg Leu Ala Asp Asp Ala Leu Ser Ala Thr Ser
        145                 150                 155 tcg tcc tcg acg acg ccg tcc acc cca cgc acc gac gac gac gag gag    590
Ser Ser Ser Thr Thr Pro Ser Thr Pro Arg Thr Asp Asp Asp Glu Glu
    160                 165                 170 tcc gcc gcc acc gac ggc gac gag tcc tcc tcc ccg gcc agc gac ctg    638
Ser Ala Ala Thr Asp Gly Asp Glu Ser Ser Ser Pro Ala Ser Asp Leu
175                 180                 185                 190 gcg ttc gaa ctg gac gtc ctg agt gac atg ggc tgg gac ctg tac tac    686
Ala Phe Glu Leu Asp Val Leu Ser Asp Met Gly Trp Asp Leu Tyr Tyr
                195                 200                 205 gcg agc ttg gcg cag ggg atg ctc atg gag cca cca tcg gcg gcg ctc    734
Ala Ser Leu Ala Gln Gly Met Leu Met Glu Pro Pro Ser Ala Ala Leu
            210                 215                 220 ggc gac gac ggt gac gcc atc ctc gcc gac gtc cca ctc tgg agc tac    782
Gly Asp Asp Gly Asp Ala Ile Leu Ala Asp Val Pro Leu Trp Ser Tyr
        225                 230                 235 tagagctcaa tcaactgtac aattttgcct cttttttctc tcttttctgg cttccgatgc   842
caaaattttg gtactgtacg gacactactt tcggtaatgt gatggaacaa gttgcaaaac   902
aaaaaaaaaa aaaaaaaaaa aaaaa                                         927

<210> SEQ ID NO 7
<211> LENGTH: 1437
<212> TYPE: DNA
<213> ORGANISM: Arabidopsis thaliana
<220> FEATURE:
<221> NAME/KEY: CDS
<222> LOCATION: (167)..(1171)

<400> SEQUENCE: 7
gctgtctgat aaaagaagaa ggaaaactcg aaaaagctac acacaagaag aagaagaaaa    60
gatacgagca agaagactaa acacgaaagc gatttatcaa ctcgaaggaa gagactttga   120
```

-continued

```
ttttcaaatt tcgtcccta tagattgtgt tgtttctggg aaggag atg gca gtt          175
                                                    Met Ala Val
                                                     1 tat gat cag agt gga gat aga aac aga aca caa att gat aca tcg agg        223
Tyr Asp Gln Ser Gly Asp Arg Asn Arg Thr Gln Ile Asp Thr Ser Arg
        5                   10                  15 aaa agg aaa tct aga agt aga ggt gac ggt act act gtg gct gag aga        271
Lys Arg Lys Ser Arg Ser Arg Gly Asp Gly Thr Thr Val Ala Glu Arg
 20                  25                  30                  35 tta aag aga tgg aaa gag tat aac gag acc gta gaa gaa gtt tct acc        319
Leu Lys Arg Trp Lys Glu Tyr Asn Glu Thr Val Glu Glu Val Ser Thr
                 40                  45                  50 aag aag agg aaa gta cct gcg aaa ggg tcg aag aag ggt tgt atg aaa        367
Lys Lys Arg Lys Val Pro Ala Lys Gly Ser Lys Lys Gly Cys Met Lys
                     55                  60                  65 ggt aaa gga gga cca gag aat agc cga tgt agt ttc aga gga gtt agg        415
Gly Lys Gly Gly Pro Glu Asn Ser Arg Cys Ser Phe Arg Gly Val Arg
             70                  75                  80 caa agg att tgg ggt aaa tgg gtt gct gag atc aga gag cct aat cga        463
Gln Arg Ile Trp Gly Lys Trp Val Ala Glu Ile Arg Glu Pro Asn Arg
 85                  90                  95 ggt agc agg ctt tgg ctt ggt act ttc cct act gct caa gaa gct gct        511
Gly Ser Arg Leu Trp Leu Gly Thr Phe Pro Thr Ala Gln Glu Ala Ala
100                 105                 110                 115 tct gct tat gat gag gct gct aaa gct atg tat ggt cct ttg gct cgt        559
Ser Ala Tyr Asp Glu Ala Ala Lys Ala Met Tyr Gly Pro Leu Ala Arg
                120                 125                 130 ctt aat ttc cct cgg tct gat gcg tct gag gtt acg agt acc tca agt        607
Leu Asn Phe Pro Arg Ser Asp Ala Ser Glu Val Thr Ser Thr Ser Ser
            135                 140                 145 cag tct gag gtg tgt act gtt gag act cct ggt tgt gtt cat gtg aaa        655
Gln Ser Glu Val Cys Thr Val Glu Thr Pro Gly Cys Val His Val Lys
        150                 155                 160 aca gag gat cca gat tgt gaa tct aaa ccc ttc tcc ggt gga gtg gag        703
Thr Glu Asp Pro Asp Cys Glu Ser Lys Pro Phe Ser Gly Gly Val Glu
165                 170                 175 ccg atg tat tgt ctg gag aat ggt gcg gaa gag atg aag aga ggt gtt        751
Pro Met Tyr Cys Leu Glu Asn Gly Ala Glu Glu Met Lys Arg Gly Val
180                 185                 190                 195 aaa gcg gat aag cat tgg ctg agc gag ttt gaa cat aac tat tgg agt        799
Lys Ala Asp Lys His Trp Leu Ser Glu Phe Glu His Asn Tyr Trp Ser
                200                 205                 210 gat att ctg aaa gag aaa gag aaa cag aag gag caa ggg att gta gaa        847
Asp Ile Leu Lys Glu Lys Glu Lys Gln Lys Glu Gln Gly Ile Val Glu
            215                 220                 225 acc tgt cag caa caa cag cag gat tcg cta tct gtt gca gac tat ggt        895
Thr Cys Gln Gln Gln Gln Gln Asp Ser Leu Ser Val Ala Asp Tyr Gly
        230                 235                 240 tgg ccc aat gat gtg gat cag agt cac ttg gat tct tca gac atg ttt        943
Trp Pro Asn Asp Val Asp Gln Ser His Leu Asp Ser Ser Asp Met Phe
245                 250                 255 gat gtc gat gag ctt cta cgt gac cta aat ggc gac gat gtg ttt gca        991
Asp Val Asp Glu Leu Leu Arg Asp Leu Asn Gly Asp Asp Val Phe Ala
260                 265                 270                 275 ggc tta aat cag gac cgg tac ccg ggg aac agt gtt gcc aac ggt tca       1039
Gly Leu Asn Gln Asp Arg Tyr Pro Gly Asn Ser Val Ala Asn Gly Ser
                280                 285                 290 tac agg ccc gag agt caa caa agt ggt ttt gat ccg cta caa agc ctc       1087
Tyr Arg Pro Glu Ser Gln Gln Ser Gly Phe Asp Pro Leu Gln Ser Leu
```

```
                295                 300                 305
aac tac gga ata cct ccg ttt cag ctc gag gga aag gat ggt aat gga    1135
Asn Tyr Gly Ile Pro Pro Phe Gln Leu Glu Gly Lys Asp Gly Asn Gly
            310                 315                 320 ttc ttc gac gac ttg agt tac ttg gat ctg gag aac taaacaaaac         1181
Phe Phe Asp Asp Leu Ser Tyr Leu Asp Leu Glu Asn
325                 330                 335 aatatgaagc ttttggatt tgatatttgc cttaatccca caacgactgt tgattctcta   1241
tccgagtttt agtgatatag agaactacag aacacgtttt ttcttgttat aaaggtgaac  1301
tgtatatatc gaaacagtga tatgacaata gagaagacaa ctatagtttg ttagtctgct  1361
tctcttaagt tgttctttag atatgtttta tgttttgtaa caacaggaat gaataataca  1421
cacttgtaaa aaaaaa                                                  1437

<210> SEQ ID NO 8
<211> LENGTH: 353
<212> TYPE: DNA
<213> ORGANISM: Oryza sativa

<400> SEQUENCE: 8
gctagcagag tagcaatcca ttccgatcca tcaaatttct cttgagaccg tagagagaga   60
gagaggcgcc aaccatggcc ggcatcatcc acaagatcga ggagaagctc acatgggcg   120 gaggcgagca caagaaggaa gacgagcaca agaaggaggg ggagcaccac aagaaggacg   180
gggagcacaa ggaaggcgtg gtggagaaga tcaaggacaa gatcaccggc gaccacggcg   240
acggcggcga gcacaaggag aagaaggaca agaagaagaa gaaggagaag aagcacggcg   300
aggagggcca ccaccacgac ggccacagca gcagcagcag cgacagcgac tgg          353

<210> SEQ ID NO 9
<211> LENGTH: 545
<212> TYPE: DNA
<213> ORGANISM: Oryza sativa

<400> SEQUENCE: 9
cgactatcat tacaaggaaa tttaagcgac cacgaagagt atgacgctgg tgaagattgg   60
tccgtggggc ggaaatggag ggtcagctca ggacatcagt gtgccaccca agaagctgtt  120
aggcgtgaca atctacagct cagatgcaat cagatccatt gccttcaact acatcggtgt  180
ggatggacag gaatatgcca ttggtccatg gggtggggc gaaggcacct ctacagagat   240
taaactgggc tcctctgagc agatcaagga gatttctgga acccatggcc cagtctatga  300
tctggctgac attgtcacct atcttaagat tgtgacaagt gctaataata catacgaggc  360
tggagtccca aatggaaagg aattcagcat tccactgcaa gactctggcc atgtcgttgg  420
attctttgga aggtctggaa cgcttatcga cgcaattggc atctacgtcc acccttgatt  480
cccagtggtc aaagaattac tacctactac catatctacg aaataatgtt ccatggtgtt  540
gttgt                                                              545

<210> SEQ ID NO 10
<211> LENGTH: 1357
<212> TYPE: DNA
<213> ORGANISM: Oryza sativa

<400> SEQUENCE: 10
agccgtggaa gtccaacctg caggctcagg ctgcagatcg cccaaggcgc acttgcctcc    60
acgatggctt gtcctcaacc gctcggaagg cgagatccaa ttggcaattt gttcaacgca  120
```

```
gggagagagg aggagactgg aacgggatca ttggacattg gttgatgaat tgcaatttgg    180
atgacgaggc cgcgagggtc agaccgtcgg agagtgagat gatggttata caagtgtact    240
agtaggacga acggtggcac cggccagaag cagcagattt tgtgcaaacg ttgagcccgc    300
aacacgtggc cggcatcgac ccgctacacg gacgcagcgc cccccccccc cccccccccg    360
cggacccacg cgggccggcc gcgtgtcgc cgtgctgccg actacgccgt cgaaatcaac     420
gcgtccgcct cgatcctccc ctgccgacgc tgtacaagtg gcgaccagaa aacaccatgt    480
agtatttgat ctcgtctaag agcaagttta atactatagt ccactattag ctccaattta   540
tttataactg atctaatagc caattcacac aataattgct tactatacta ttaatatatg   600
gtctcacatg tcatacacat attccgtctt ggagttcgtg ctgcagctgg ctacagatct   660
gtagcccgct gctcttctct ctcagagcga gtataatagt acaaactgga ctggcgatag   720
gagaaacacg tcagctacag tgttgagctg gatgagtgag aagaggagag agagtgagag   780
tgggcgacaa ttttatcgcc ggctctagca ccagcttcga gagaaaagtg gtgagcgcag   840
aggttgtgag ctgcatgtgt gagacgaagc ttaagttatt ttattatgat gtgaagttga   900
tgggtccagc gttgcaggtc atttattgta ttcacaagat gcaagagag ctactagctg    960 agttggatgg aattaacgcc ggctgtctac gctactatta accttgctct catctttat   1020 ctcatcaaaa tatatttata gctggctaat agtctgctat cgtacctgct ctaatgcata  1080
cgttttttct ctctgtggca aaacggttgg tgcgttacac ggggtgcacg aagccatgca  1140
tcaccctgct caacccgtct ccttttttag cctaatcttt tcctccttat ccgatgggcc  1200
ttccgtttct caagacaccc ccacaccgcc ccggccctct ataaatacca accacgacga  1260
gccaagcgaa catcaccaca gctagatcat tagcaatcca ttccgatcca tcaaatttct  1320
cttgagaccg tagagagaga gagaggcgcc aaccatg                            1357

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 11
ccattggatc cagccgtgga agtccaac                                         28

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 12
gccggggatc cttggcgcct ctctctct                                         28
```